US00RE50824E

(19) United States
(12) Reissued Patent
Igarashi

(10) Patent Number: US RE50,824 E
(45) Date of Reissued Patent: Mar. 17, 2026

(54) BLOOD COMPONENT SAMPLING CASSETTE, BLOOD SAMPLING CIRCUIT SET, AND BLOOD COMPONENT SAMPLING SYSTEM

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

(21) Appl. No.: 18/594,959

(22) Filed: Mar. 4, 2024

Related U.S. Patent Documents

Reissue of:
(64) Patent No.: 11,752,243
Issued: Sep. 12, 2023
Appl. No.: 16/332,473
PCT Filed: Sep. 12, 2017
PCT No.: PCT/JP2017/032886
§ 371 (c)(1),
(2) Date: Mar. 12, 2019
PCT Pub. No.: WO2018/051982
PCT Pub. Date: Mar. 22, 2018

(30) Foreign Application Priority Data

Sep. 14, 2016 (JP) ..... 2016-179107

(51) Int. Cl.
*A61M 1/02* (2006.01)
*A61M 1/36* (2006.01)
(Continued)

(52) U.S. Cl.
CPC ..... *A61M 1/0236* (2014.02); *A61M 1/0209* (2013.01); *A61M 1/0245* (2013.01);
(Continued)

(58) Field of Classification Search
CPC ..... A61M 1/0245; A61M 1/362261; A61M 1/362266; A61M 1/362264;
(Continued)

(56) References Cited

U.S. PATENT DOCUMENTS 5,429,485 A * 7/1995 Dodge ..... A61M 5/142 604/152
6,481,980 B1 * 11/2002 Vandlik ..... A61M 1/30 417/313
(Continued)

FOREIGN PATENT DOCUMENTS

DE 102014102598 A1 8/2015
WO 2009029677 A1 6/2009
WO WO 2017/142003 A1 * 8/2017

*Primary Examiner* — Elizabeth L Mckane
(74) *Attorney, Agent, or Firm* — Sheridan Ross P.C.

(57) ABSTRACT

A blood component sampling cassette which can be more efficiently manufactured at lower cost as compared to a typical cassette, a blood sampling circuit set, and a blood component sampling system. A blood component sampling cassette (22) includes a cassette main body (23) made of a soft material to which heat sterilization is applicable. The cassette main body (23) is provided with a retransfusion line (44). The retransfusion line (44) is provided with a reservoir (47) configured to temporarily store a blood component to be returned to a blood donor. The reservoir (47) is pressed by a retransfusion pump (49) to discharge the blood component from the reservoir (47).

20 Claims, 17 Drawing Sheets

(51) Int. Cl.

| | |
|---|---|
| ***A61M 1/38*** | (2006.01) |
| ***A61M 60/104*** | (2021.01) |
| ***A61M 60/279*** | (2021.01) |
| ***A61M 60/39*** | (2021.01) |
| ***A61M 60/441*** | (2021.01) |
| ***A61M 60/554*** | (2021.01) |
| ***A61M 60/847*** | (2021.01) |
| ***A61M 60/851*** | (2021.01) |
| ***B04B 5/04*** | (2006.01) |
| ***B04B 11/02*** | (2006.01) |

(52) U.S. Cl.

CPC ..... *A61M 1/3621* (2013.01); *A61M 1/36224* (2022.05); *A61M 1/362261* (2022.05); *A61M 1/362262* (2022.05); *A61M 1/362264* (2022.05); *A61M 1/362266* (2022.05); *A61M 1/3693* (2013.01); *A61M 1/38* (2013.01); *A61M 60/104* (2021.01); *A61M 60/279* (2021.01); *A61M 60/39* (2021.01); *A61M 60/441* (2021.01); *A61M 60/554* (2021.01); *A61M 60/847* (2021.01); *A61M 60/851* (2021.01); *B04B 5/0442* (2013.01); *B04B 11/02* (2013.01); *A61M 2202/0415* (2013.01); *A61M 2202/0427* (2013.01); *A61M 2202/0429* (2013.01); *A61M 2202/0439* (2013.01); *A61M 2205/12* (2013.01); *A61M 2205/123* (2013.01); *A61M 2205/3331* (2013.01)

(58) Field of Classification Search

CPC ..... A61M 1/3693; A61M 1/36224; A61M 1/0209; A61M 1/3621; A61M 1/362262; A61M 1/0236; A61M 1/38; A61M 60/851; A61M 60/279; A61M 60/39; A61M 60/847; A61M 60/104; A61M 60/554; A61M 60/441; A61M 2205/3331; A61M 2205/0439; A61M 2205/0427; A61M 2205/0429; A61M 2205/0415; A61M 2205/12; A61M 2205/123; B04B 5/0442; B04B 11/02

See application file for complete search history.

(56) References Cited

U.S. PATENT DOCUMENTS

| | | | | |
|---|---|---|---|---|
| 2004/0082899 | A1* | 4/2004 | Mathias | A61M 1/0209 604/6.16 |
| 2007/0253463 | A1* | 11/2007 | Perry | A61M 1/369 374/208 |
| 2009/0060753 | A1* | 3/2009 | Jones | F04B 7/00 417/46 |
| 2013/0040797 | A1* | 2/2013 | Lindner | A61M 1/3696 494/10 |
| 2016/0367742 | A1 | 12/2016 | Häcker | |

* cited by examiner

BLOOD COMPONENT SAMPLING CASSETTE, BLOOD SAMPLING CIRCUIT SET, AND BLOOD COMPONENT SAMPLING SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a broadening reissue of U.S. Pat. No. 11,752,243, which was assigned U.S. patent application Ser. No. 16/332,473 and filed Mar. 12, 2019, which is a national stage application under 35 U.S.C. 371 and claims the benefit of PCT Application No. PCT/JP2017/032886 having an international filing date of Sep. 12, 2017, which designated the United States, which PCT application claimed the benefit of Japanese Patent Application No. 2016-179107, filed Sep. 14, 2016, the disclosures of which are incorporated herein by reference in their entirety.*

TECHNICAL FIELD

The present disclosure relates to a biological component sampling cassette attached to a separation device configured to separate a biological component from liquid containing at least one biological component. Specifically, the present disclosure relates to a blood component sampling cassette attached to a blood component separation device, a blood sampling circuit set, and a blood component sampling system.

BACKGROUND ART

In recent blood donation, blood component sampling (apheresis) with a less burden on a blood donor body has been performed in addition to whole blood sampling for sampling whole blood from a blood donor. Blood component sampling is a blood sampling method using a blood component sampling system (an apheresis system) to sample only specific blood components from the whole blood and return the remaining components to the body of the blood donor.

Patent Document 1 discloses a blood component sampling system configured to centrifuge whole blood extracted from a blood donor to sample platelet. This blood component sampling system includes a blood sampling circuit set forming a circuit in which blood or blood components to be processed flow, and a centrifuge (a blood component separation device) attached to the blood sampling circuit set. The blood sampling circuit set includes a blood sampling line having a blood sampling needle, a band-shaped channel (a separator) to which the whole blood is introduced, a plurality of bags configured to contain the blood components and the like, and a cassette connected to these elements through a plurality of tubes. The cassette is provided with a plurality of flow paths including, for example, a line for introducing the blood from the blood donor, a line for transferring the blood component to each bag, and a retransfusion line for returning, to the blood donor, the blood components not to be sampled. Upon use, the cassette is attached to an attachment section provided at the blood component separation device.

PRIOR ART DOCUMENT

[PATENT DOCUMENT 1] Japanese Laid-Open Patent Publication No. 2013-514863

SUMMARY OF INVENTION

Technical Problem

A typical cassette has been made of hard resin, such as PET, not resistant to high heat in autoclave sterilization (so-called heat sterilization), and therefore, EOG sterilization has been performed as sterilization processing in manufacturing. EOG sterilization has problems such as great care and a high cost for sterilization for reasons such as that special processing gas is needed as compared to autoclave sterilization. Moreover, the typical cassette has been molded by a large-scale injection molding method, leading to a problem such as a high manufacturing cost.

The present disclosure has been made in view of the above-described problems, and an object of the present invention is to provide a blood component sampling cassette which can be more efficiently manufactured at lower cost as compared to a typical cassette, a blood sampling circuit set, a blood component sampling system.

Solution to Problem

For accomplishing the above-described object, the present disclosure relates to a biological component sampling cassette including a cassette main body provided with a plurality of flow paths and configured to be attachable to a separation device configured to separate a biological component from liquid containing at least one biological component. The cassette main body is made of a soft material to which heat sterilization is applicable. The plurality of flow paths include an introduction line configured to introduce the liquid, a biological component transfer line configured to transfer, to a sampling container, the biological component obtained by separation processing of the liquid, and a return line configured to transfer liquid other than the biological component obtained by the separation processing. The return line is provided with a reservoir configured to temporarily store the liquid to be returned. The reservoir is configured to be expandable/contractable, and is pressed by a return pump provided at the separation device to discharge the liquid from the reservoir. Moreover, the biological component is blood or a cultured or sampled cell.

According to the biological component sampling cassette of the present disclosure having the above-described configuration, easier autoclave sterilization as compared to other types of sterilization processing (e.g., EOG sterilization) is applicable as sterilization processing upon manufacturing, leading to efficient manufacturing. Further, the cassette main body is made of the soft material, and therefore, the cassette can be manufactured at lower cost as compared to the typical cassette made of the hard resin by large-scale injection molding. Further, the cassette main body is provided with the reservoir pressed by the return pump of the separation device to discharge the liquid. Thus, in the separation device, it is not necessary to separately ensure a location for disposing the reservoir and a location for providing the pump, and therefore, device layout simplification and compactification are easily realized.

In the above-described biological component sampling cassette, the cassette main body may have a sensor pressing section configured to press a reservoir pressure sensor equipped at the separation device, thereby detecting an inner pressure of the reservoir.

Thus, the inner pressure of the reservoir can be detected with a simple configuration.

In the above-described biological component sampling cassette, the sensor pressing section may be provided at the return line.

Thus, the inner pressure of the reservoir can be more precisely detected.

In the above-described biological component sampling cassette, the reservoir may be expanded in a normal state.

Thus, a desired reservoir capacity can be easily ensured.

Moreover, the present disclosure relates to a biological component sampling circuit set including a biological component sampling cassette having a cassette main body provided with a plurality of flow paths and configured to be attachable to a separation device configured to separate a biological component from liquid containing at least one biological component, a separation processing section connected to the biological component sampling cassette through a tube and having a processing chamber configured to separate the liquid into multiple biological components by actuation of the separation device, and a bag connected to the biological component sampling cassette through a tube. The cassette main body is made of a soft material to which heat sterilization is applicable. The plurality of flow paths include an introduction line configured to introduce the liquid, a biological component transfer line configured to transfer, to a sampling container, the biological component obtained by separation processing of the liquid, and a return line configured to transfer liquid other than the biological component obtained by the separation processing. The return line is provided with a reservoir configured to temporarily store the liquid to be returned. The reservoir is configured to be expandable/contractable, and is pressed by a return pump provided at the separation device to discharge the liquid from the reservoir.

According to the biological component sampling circuit set, the circuit set can be efficiently manufactured at low cost, and the device layout of the separation device can be simplified.

Further, the present disclosure relates to a biological component sampling system including a separation device configured to separate a biological component from liquid containing at least one biological component, and a biological component sampling cassette configured to be attachable to the separation device. The biological component sampling cassette includes a cassette main body provided with a plurality of flow paths. The cassette main body is made of a soft material to which heat sterilization is applicable. The plurality of flow paths include an introduction line configured to introduce the liquid, a biological component transfer line configured to transfer, to a sampling container, the biological component obtained by separation processing of the liquid, and a return line configured to transfer liquid other than the biological component obtained by the separation processing. The return line is provided with a reservoir configured to temporarily store the liquid to be returned. The reservoir is configured to be expandable/contractable, and is pressed by a return pump provided at the separation device to discharge the liquid from the reservoir.

According to the biological component sampling system, the biological component sampling system can be efficiently manufactured at low cost, and the device layout of the separation device can be simplified.

In the above-described biological component sampling system, the return pump equipped at the separation device may have a pressing plate configured to press the reservoir in a thickness direction.

By the return pump (a pressing plate type pump) having such a configuration, desired solution transfer performance (a flow rate) can be easily obtained.

In the above-described biological component sampling system, the separation device may include a reservoir pressure detection mechanism configured to detect the inner pressure of the reservoir, and a control section configured to control operation of the pump based on the pressure detected by the reservoir pressure detection mechanism.

With this configuration, a return speed (the flow rate) can be accurately controlled.

In the above-described biological component sampling system, the control section may control operation of the pump such that the inner pressure of the reservoir reaches a predetermined target pressure.

With this configuration, the return speed can be maintained substantially constant.

In the above-described biological component sampling system, the cassette main body may have a sensor pressing section configured to press the reservoir pressure detection mechanism.

Advantageous Effects of Invention

According to the present disclosure, the cassette can be more efficiently manufactured at lower cost as compared to the typical cassette.

DESCRIPTION OF EMBODIMENTS

Figure 1:
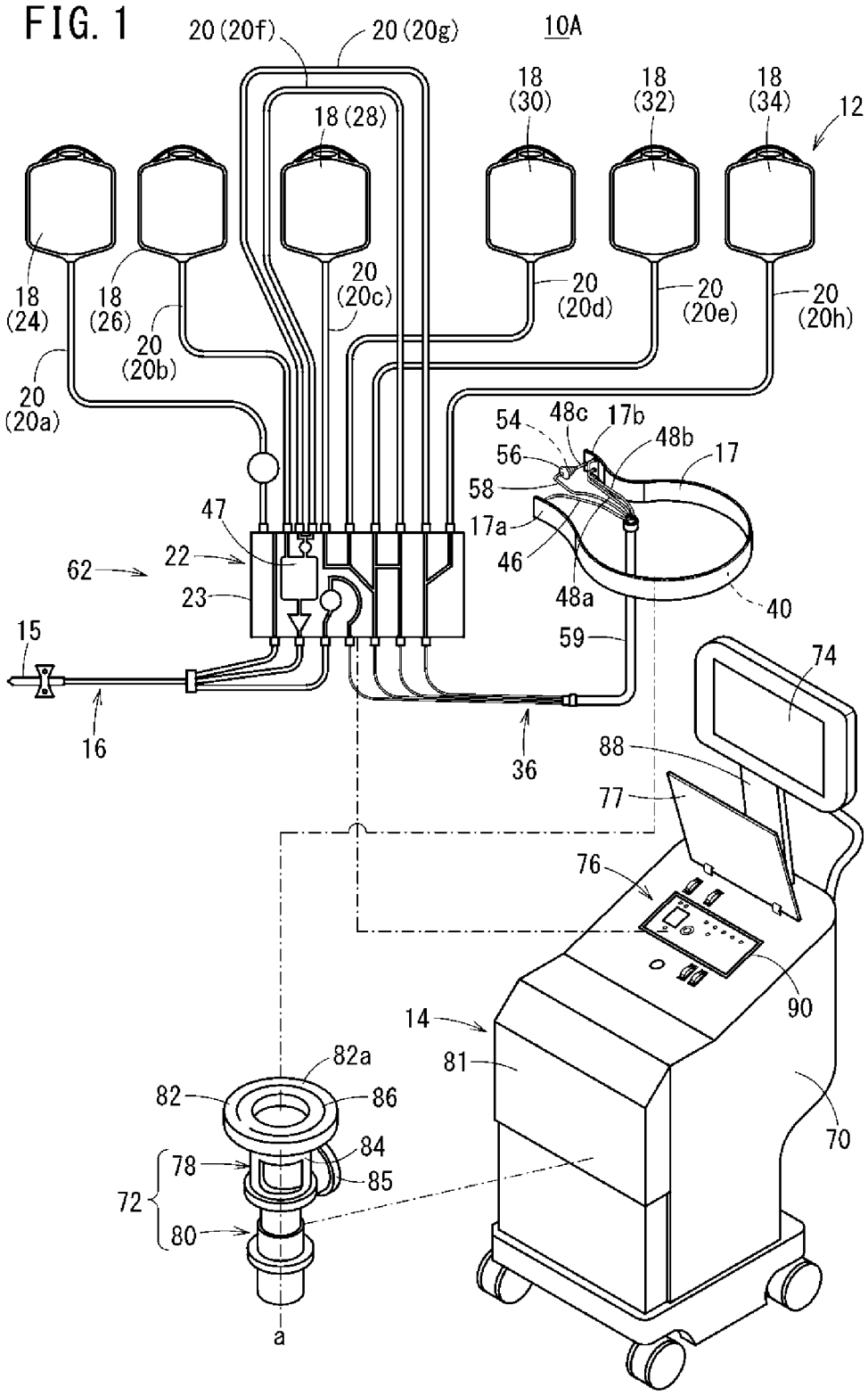
FIG. 1 is a schematic view of a blood component sampling system of a first embodiment of the present disclosure.

Multiple preferable embodiments of the present disclosure will be described below with reference to the attached drawings. Note that in a second embodiment, the same reference numerals are used to represent identical or similar elements to those of a first embodiment, and detailed description thereof will not be repeated.

First Embodiment

In FIG. 1, a blood component sampling system 10A is configured as a blood apheresis system, which continuously extracts blood (whole blood) from a blood donor to centrifuge the blood outside a body, thereby sampling specific blood components (platelet, red blood cells, plasma in the present embodiment) while returning, to the blood donor, blood components not to be sampled.

First, the blood component sampling system 10A illustrated in FIG. 1 will be schematically described. This blood component sampling system 10A includes a blood sampling circuit set 12 configured to store and circulate the blood components, and a centrifuge 14 (a blood component separation device) configured to apply centrifugal force to the blood sampling circuit set 12. The blood sampling circuit set 12 has a channel 17 (a blood processing section) as a primary separator configured such that the whole blood extracted from the blood donor is introduced and centrifuged to the multiple blood components. The centrifuge 14 has a rotor 78 configured to apply the centrifugal force to the channel 17. An attachment groove 86 extending in a circumferential direction about the rotation axis "a" of the rotor 78 is formed at an upper surface 82a of the rotor 78, and the channel 17 is attachable to the attachment groove 86.

Next, the blood sampling circuit set 12 and the centrifuge 14 will be described in detail.

The blood sampling circuit set 12 is discarded after every use to prevent contamination and keep sanitation. The blood sampling circuit set 12 includes a blood sampling/retransfusion section 16 having a blood sampling needle 15, the channel 17, a plurality of bags 18, and a blood component sampling cassette 22 (hereinafter referred to as a "cassette 22") connected to these elements through a plurality of tubes. The plurality of bags 18 includes an ACD solution bag 24, an air bag 26, a platelet preservation solution bag 28, a PPP bag 30, a platelet bag 32, and a red blood cell bag 34.

The blood sampling/retransfusion section 16 is connected to the ACD solution bag 24 and the channel 17 through the cassette 22. During use of the blood sampling circuit set 12, an ACD solution as an anticoagulant agent is, as default operation, supplied from the ACD solution bag 24 to the channel 17, and in this manner, coagulation of the whole blood is suppressed.

The channel 17 is connected to the cassette 22 through a channel connection line 36. Meanwhile, the plurality of bags 18 are connected to the cassette 22 through the plurality of tubes 20.

The channel 17 is formed in a belt-shaped bag. The channel 17 is attached to the attachment groove 86 formed at the rotor 78 of the centrifuge 14, and is configured to allow introduction and flowing in/out of the blood. Further, the channel 17 is a soft bag having, on the inside thereof, a first chamber 40 (a processing chamber) to which the whole blood of the blood donor is supplied, and can be easily bent, folded, and rounded. The first chamber 40 extends from one end portion 17a to another end portion 17b of the channel 17.

The one end portion 17a of the channel 17 is coupled to an introduction tube 46 forming part of the channel connection line 36. The introduction tube 46 is connected to the cassette 22. During centrifugation processing, the whole blood introduced to the first chamber 40 is centrifuged by the centrifugal force while circulating from the one end portion 17a to the other end portion 17b.

In blood component sampling by means of the blood sampling circuit set 12, the whole blood extracted from the blood donor through the blood sampling needle 15 flows from the one end portion 17a connected to the introduction tube 46 to the first chamber 40 of the channel 17 attached to the attachment groove 86. The inflow whole blood circulates toward the other end portion 17b along an extension direction of the channel 17. The whole blood receives the centrifugal force accompanied by rotation of the rotor 78, and therefore, is centrifuged while circulating. In the case of the present embodiment, the whole blood is, by centrifugation, separated into plasma (platelet poor plasma: PPP) as a light specific gravity component (a supernatant component), red blood cells (concentrated red cells) as a heavy specific gravity component (a sedimentation component), and buffy coat (BC) as an intermediate specific gravity component.

The other end portion 17b of the channel 17 is connected to first to third lead tubes 48a to 48c. The first lead tube 48a and the second lead tube 48b are connected to the cassette 22. The red blood cells separated by centrifugation in the first chamber 40 are introduced to the cassette 22 through the first lead tube 48a. Further, the plasma generated in the first chamber 40 is introduced to the cassette 22 through the second lead tube 48b.

The third lead tube 48c is connected to a concentrator 56 as a secondary separator having a second chamber 54. The buffy coat generated in the first chamber 40 by centrifugation of the whole blood is introduced to the concentrator 56 through the third lead tube 48c. The buffy coat contains a white blood cell component and platelet-rich plasma (a platelet-containing component).

The concentrator 56 is configured to introduce the buffy coat from the channel 17 to the second chamber 54 and further centrifuge the buffy coat by the centrifugal force accompanied by rotation of the rotor 78. This concentrator 56 is formed in a conical shape with multiple steps. In a state in which the concentrator 56 is attached to the rotor 78, a top side of the conical shape is disposed further from the centrifugal center, and a bottom side of the conical shape is disposed closer to the centrifugal center.

The concentrator 56 separates the buffy coat into white blood cells as a heavy specific gravity component and platelet as a light specific gravity component (more specifically, a platelet-containing component containing plasma and platelet). The white blood cells are captured by the multiple steps formed at the concentrator 56. The platelet flows out to a relay tube 58 connected to an outlet (the bottom side) of the concentrator 56, and is introduced to the cassette 22.

Note that the introduction tube 46, the first lead tube 48a, the second lead tube 48b, and the relay tube 58 are bundled by a bundling sheath 59. In the present embodiment, the channel connection line 36 includes the introduction tube 46, the first to third lead tubes 48a to 48c, the concentrator 56, and the relay tube 58.

The ACD solution bag 24 is a bag configured to contain the ACD solution as the anticoagulant agent, and is connected to the cassette 22 through a tube 20a. The air bag 26 is a bag configured to contain air discharged from a later-described reservoir 47 at a later-described priming process in retransfusion processing, and is connected to the cassette 22 through a tube 20b.

The platelet preservation solution bag 28 is a bag configured to contain a platelet preservation solution (a PAS solution), and is connected to the cassette 22 through a tube 20c. The PPP bag 30 is a bag configured to contain the plasma obtained by centrifugation, and is connected to the cassette 22 through a tube 20d.

The platelet bag 32 is a bag configured to contain the platelet obtained by centrifugation, and is connected to the cassette 22 through a tube 20e. The red blood cell bag 34 is a bag configured to contain the red blood cells obtained by centrifugation, and is connected to the cassette 22 through a tube 20h.

Figure 3:
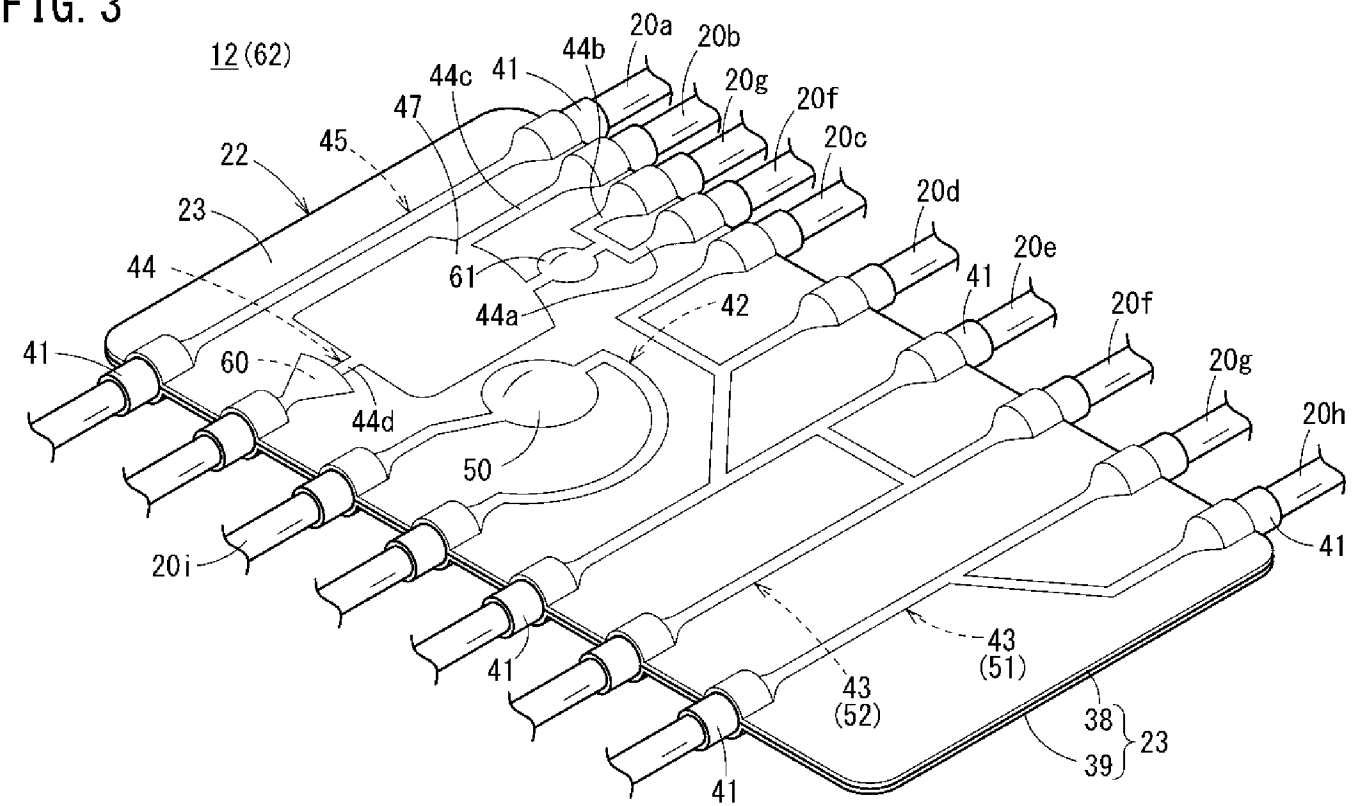
FIG. 3 is a perspective view of a blood component sampling cassette of a first embodiment of the present invention.

In FIG. 3, the cassette 22 includes a cassette main body 23 having a plurality of flow paths. The cassette main body 23 has a first sheet 38 and a second sheet 39, these sheets being made of a soft material to which autoclave sterilization is applicable. The first sheet 38 and the second sheet 39 overlap with each other in a thickness direction, and are bonded to each other.

The soft material which forms the first sheet 38 and the second sheet 39 and to which autoclave sterilization is applicable means that the soft material exhibits heat resistance against heat (e.g. 121° C.) of autoclave sterilization for equal to or longer than a predetermined period of time and exhibits water vapor permeability allowing introduction of water vapor as processing gas to the flow paths in the cassette 22. Such a soft material includes, for example, vinyl chloride and polyolefin.

The plurality of flow paths are formed between the first sheet 38 and the second sheet 39. The way of bonding the first sheet 38 and the second sheet 39 includes, for example, fusion (high-frequency fusion, thermal fusion, and the like) and adhesion. Further, the cassette 22 has a plurality of port members 41 arranged at a peripheral edge portion of the cassette main body 23, and tubes (the tubes 20 and the like) are each connected to these port members 41.

Figure 2:
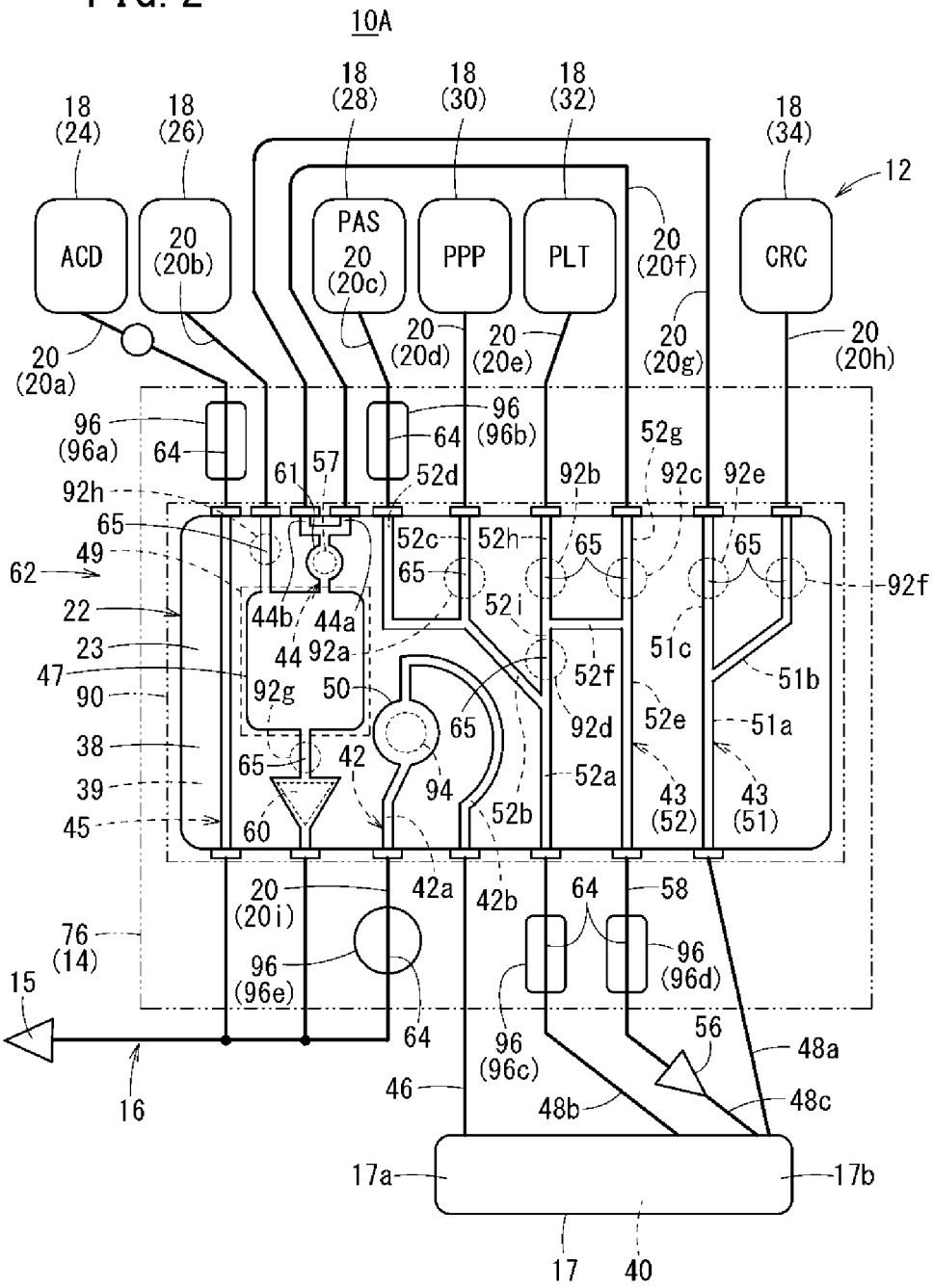
FIG. 2 is a circuit configuration diagram of the blood component sampling system illustrated in FIG. 1.

As illustrated in FIG. 2, the plurality of flow paths formed at the cassette main body 23 at least include an introduction line 42 configured to introduce the blood sampled from the blood donor, a blood component transfer line 43 configured to transfer, to sampling containers (the PPP bag 30, the platelet bag 32, the red blood cell bag 34), the blood components obtained by the processing of separating the blood, and a retransfusion line 44 configured to transfer, to the blood donor, the blood components not to be sampled. In the present embodiment, the plurality of flow paths further include an ACD solution line 45 configured to transfer the ACD solution to the blood sampling/retransfusion section 16.

An inflow side (a flow path element 42a) of the introduction line 42 is connected to a tube of the blood sampling/retransfusion section 16. An outflow side (a flow path element 42b) of the introduction line 42 is connected to the introduction tube 46 connected to the channel 17. Thus, the blood sampling/retransfusion section 16 and the channel 17 are connected through the introduction line 42. Moreover, an expandable/contractable balloon section 50 is provided on the introduction line 42. The balloon section 50 is a portion configured to press a later-described centrifugal pressure sensor 94 (see FIG. 6) provided at the centrifuge 14. The first sheet 38 and the second sheet 39 partially form a wall of the balloon section 50. A lumen of the balloon section 50 communicates with the flow path element 42a and the flow path element 42b.

The blood component transfer line 43 has a first line 51 and a second line 52 independent from each other. A flow path element 51a forming an inflow side of the first line 51 is connected to the first lead tube 48a connected to the channel 17. The first line 51 includes, on an outflow side thereof, flow path elements 51b, 51c branched from the flow path element 51a. The flow path element 51b is connected to the tube 20h connected to the red blood cell bag 34. The flow path element 51c is connected to a tube 20g connected to the reservoir 47. Thus, the red blood cells separated in the channel 17 can be transferred to the red blood cell bag 34 through the flow path elements 51a, 51b, and can be transferred to the reservoir 47 through the flow path elements 51a, 51c.

The second line 52 is connected to the second lead tube 48b, the relay tube 58, and the tubes 20c to 20f. Specifically, the second line 52 has a flow path element 52a connected to the second lead tube 48b, a flow path element 52b branched from the flow path element 52a, a flow path element 52c connected to the tube 20d connected to the PPP bag 30 and continuing to the flow path element 52b, and a flow path element 52d connected to the tube 20c connected to the platelet preservation solution bag 28 and continuing to the flow path element 52b. The second lead tube 48b is connected to an inflow side of the flow path element 52a. The tube 20c is connected to an inflow side of the flow path element 52d.

The second line 52 further has a flow path element 52e connected to the relay tube 58, a flow path element 52f and a flow path element 52g branched from the flow path element 52e, a flow path element 52h continuing to the flow path element 52f and connected to the tube 20e connected to the platelet bag 32, and a flow path element 52i branched from the flow path element 52a and continuing to the flow path element 52f and the flow path element 52h. The tube 20f connected to the reservoir 47 is connected to the flow path element 52g. The relay tube 58 is connected to an inflow side of the flow path element 52e.

The plasma separated in the channel 17 can be transferred to the PPP bag 30 through the flow path elements 52a to 52c in the cassette 22. Further, the plasma separated in the channel 17 can be transferred to the reservoir 47 through the flow path elements 52a, 52i, 52f, 52g in the cassette 22. The platelet separated in the channel 17 can be transferred to the platelet bag 32 through the flow path elements 52e, 52f, 52h in the cassette 22. The platelet preservation solution can be transferred to the platelet bag 32 through the flow path elements 52d, 52b, 52i, 52h in the cassette 22.

The reservoir 47 is provided at the retransfusion line 44. The reservoir 47 is a container configured to temporarily store the blood components to be returned to the blood donor. In the centrifugation processing, the red blood cells and the plasma are introduced to the reservoir 47 through the tubes 20f, 20g, and are temporarily stored in the reservoir 47. Uncollected blood components are returned from the reservoir 47 to the blood donor during or after the centrifugation processing.

The first sheet 38 and the second sheet 39 partially form the reservoir 47, and the reservoir 47 is configured to be expandable/contractable. Specifically, the reservoir 47 is expandable/contractable in the thickness direction of the cassette main body 23. The blood components in the reservoir 47 are discharged in such a manner that the reservoir 47 is pressed by a retransfusion pump 49 provided at a cassette holding section 90 (see FIG. 4) of the centrifuge 14. In the present embodiment, the reservoir 47 is expanded in a normal state. The capacity of the reservoir 47 is set to, e.g., 30 to 100 mL, and preferably 50 to 70 mL.

As illustrated in FIG. 3, the reservoir 47 is connected to the tube 20f through a flow path element 44a, and is connected to the tube 20g through a flow path element 44b. A sensor pressing section 61 configured to press a reservoir pressure sensor 57 (see FIG. 4) provided at the centrifuge 14 is provided at a flow path joint between the flow path element 44a and the flow path element 44b. The sensor pressing section 61 is similarly configured as in the above-described balloon section 50. That is, the first sheet 38 and the second sheet 39 partially form the sensor pressing section 61, and the sensor pressing section 61 is configured in a balloon shape expandable/contractable according to an inner pressure. Moreover, the reservoir 47 is connected to the air bag 26 through a flow path element 44c and the tube 20b.

In FIG. 2, the blood sampling/retransfusion section 16 is connected to an outflow side of the retransfusion line 44. A filter member 60 configured to remove a foreign material, such as coagulated blood clots, contained in the blood components having passed through the reservoir 47 is disposed on the flow path of the retransfusion line 44 in the cassette main body 23. In the retransfusion line 44, the filter member 60 is disposed on the downstream side of the reservoir 47.

In the present embodiment, the flow paths (including the reservoir 47) provided at the cassette 22 may be flow paths configured to open in the normal state. Thus, even when a positive pressure is not applied, flow path formation portions of the first sheet 38 and the second sheet 39 expand in a shape raised in the thickness direction of the cassette 22. Note that the flow paths provided at the cassette 22 may be flow paths configured to close when the positive pressure is not applied and to open when the positive pressure is applied. In the case of such flow paths, when the positive pressure is not applied, the flow path formation portions of the first sheet 38 and the second sheet 39 are substantially flat, and when the positive pressure is applied, the flow path formation portions of the first sheet 38 and the second sheet 39 expand in the raised shape.

Of the blood sampling circuit set 12, an assembly including the cassette 22 and the tubes (the tubes 20 and the like) connected to the cassette 22 will be hereinafter referred to as a "cassette/tube assembly 62."

Of the tubes connected to the cassette main body 23, the tubes (the inflow-side tubes) (excluding the tube 20g) connected to inflow sides of the plurality of flow paths are, in FIG. 2, provided with pump operation sections 64 on which pumps 96 provided at the centrifuge 14 operate. Each pump operation section 64 is disposed on the inflow side of an associated one of the flow paths formed in the cassette 22. By driving of each pump 96, the positive pressure is applied to a downstream side of the pump operation section 64 in an associated one of the flow paths formed in the cassette main body 23.

In the present embodiment, the tube 20a connected to an inflow side of the ACD solution line 45, a tube 20i connected to the inflow side of the introduction line 42, and the tubes (the tube 20c, the second lead tube 48b, and the relay tube 58) connected to an inflow side of the second line 52 are provided with the pump operation sections 64. The pump operation sections 64 are portions of the tubes 20a, 20c, 20i, the second lead tube 48b, and the relay tube 58 attached (contacting) to the pumps 96. The pump operation sections 64 may be in the form of a normal tube, and do not necessarily have a special configuration.

The cassette 22 is provided with a plurality of clamp operation sections 65 on which a plurality of clamps 92 provided at the centrifuge 14 operate. When the cassette 22 is attached to the centrifuge 14, each clamp operation section 65 contacts or faces an associated one of the clamps 92. Specifically, the clamp operation sections 65 are each provided at portions of the cassette 22 forming the flow path elements 51b, 51c of the first line 51, portions of the cassette 22 forming the flow path elements 52c, 52g, 52h, 52i of the second line 52, and portions of the cassette 22 forming the flow path elements 44c, 44d (see FIG. 3) of the retransfusion line 44.

Note that the configuration of each flow path formed in the cassette 22, the number of provided bags, and arrangement of the provided bags are not limited to those of the illustrated configuration described above, and may be modified according to the types of blood components to be sampled and the method for using these components. For example, when no red blood cells are sampled, the red blood cell bag 34 may be omitted. Further, the ACD solution bag 24 may be detached from the cassette 22 in a default state, and upon use by a user, may be connected to the cassette 22 in such a manner that the tube 20a with a connection needle is connected to the ACD solution bag 24.

In FIG. 1, the centrifuge 14 is a device repeatedly used in blood component sampling, and is equipped at medical facilities, blood sampling vehicles, and the like. The centrifuge 14 includes a box-shaped device main body 70 formed relatively long in a height direction, a monitor 74 supported by a support column 88 protruding upward from an upper rear side of the device main body 70, an attachment section 76 configured to allow attachment of the cassette/tube assembly 62 of the blood sampling circuit set 12, a cover body 77 configured to open/close and to cover the attachment section 76 when closed, a centrifugal unit 72 housed in the device main body 70, and a door 81 configured to open/close on a front side of the device main body 70.

The device main body 70 has the function of hanging and holding the plurality of bags 18 of the blood sampling circuit set 12 and controlling centrifugation of the blood extracted into the blood sampling circuit set 12.

The monitor 74 is, for example, of a touch panel type, and functions not only as a display unit configured to display, e.g., an operation state of the device main body 70 upon blood centrifugation, but also an input unit configured to input an instruction for operating the device main body 70.

Figure 4:
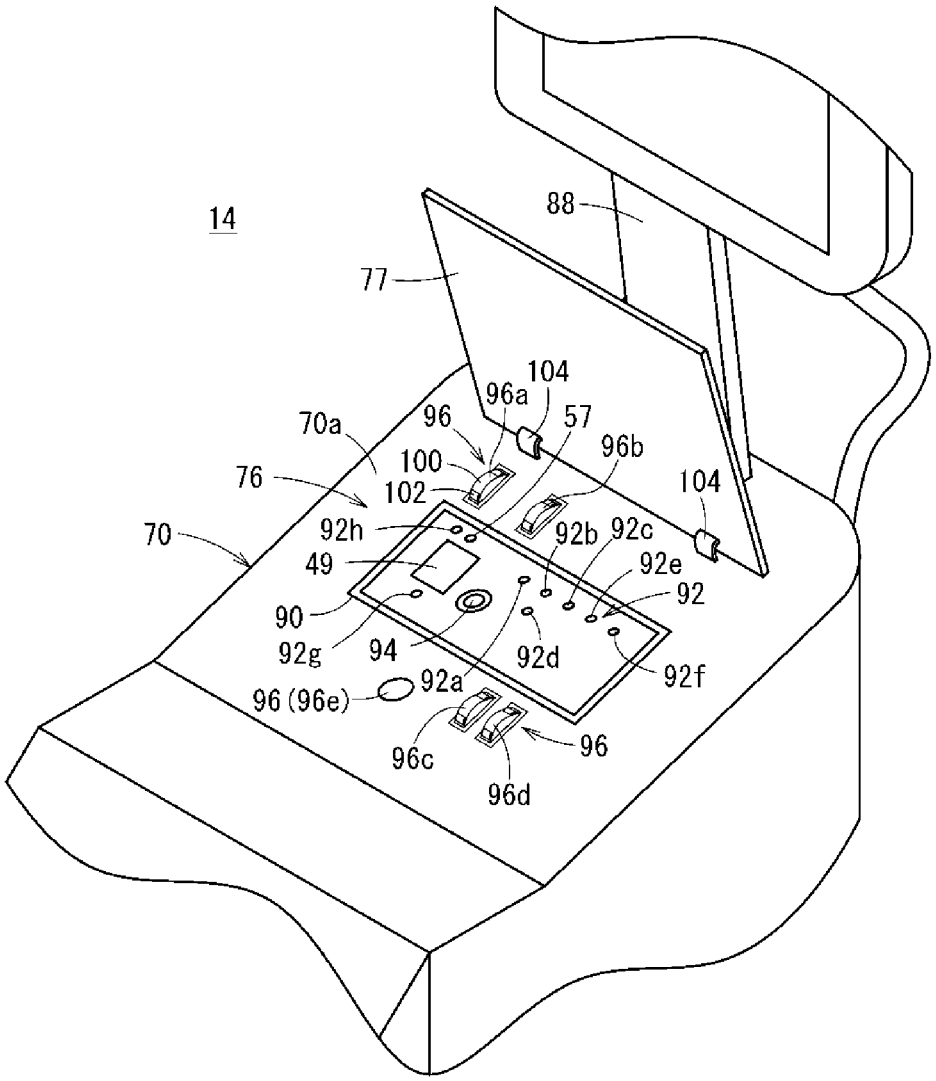
FIG. 4 is a perspective view of a configuration of an attachment section of a centrifuge in the blood component sampling system illustrated in FIG. 1.

In FIG. 4, the attachment section 76 is disposed on an upper side of the device main body 70. In the present embodiment, the attachment section 76 has the cassette holding section 90 configured to hold the cassette 22, and the plurality of clamps 92 (92a to 92h) configured to press the clamp operation sections 65 provided at the cassette 22. The attachment section 76 further has the centrifugal pressure sensor 94 configured to detect a centrifugal pressure, the pumps 96 operating on the tubes connected to the inflow sides of the plurality of flow paths provided at the cassette 22, the retransfusion pump 49 operating on the reservoir 47, and the reservoir pressure sensor 57 (a reservoir pressure detection mechanism) configured to detect the inner pressure of the reservoir 47.

For example, the cassette holding section 90 may include a plurality of pins, and may be configured to hold the cassette 22 when the plurality of pins are inserted into respective holes provided at a peripheral edge portion of the cassette 22. Alternatively, the cassette holding section 90 may be configured to hold the cassette 22 by sandwiching the peripheral edge portion of the cassette 22. When the cover body 77 is closed in a state in which the cassette 22 is held by the cassette holding section 90, the cassette 22 is sandwiched between a housing of the device main body 70 and the cover body 77.

The plurality of clamps 92 (92a to 92h) are provided at the cassette holding section 90. Each clamp 92 is operable to move back and forth in the thickness direction (a direction indicated by an arrow A of FIG. 5A) of the cassette 22 in a state in which the clamp 92 is held by the cassette holding section 90, and is disposed corresponding to an associated one of the plurality of clamp operation sections 65 provided at the cassette 22.

Figure 5A:
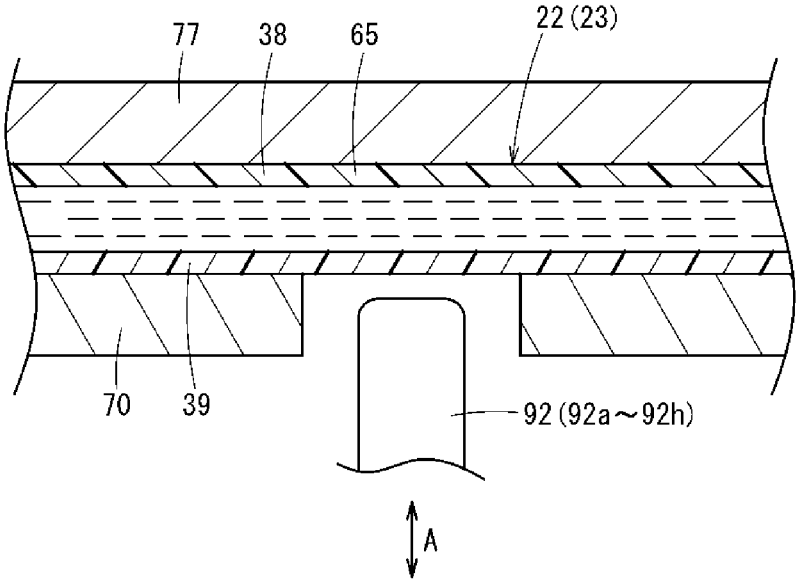
FIG. 5A is a first view for describing a function of a clamp provided at the centrifuge.
Figure 5B:
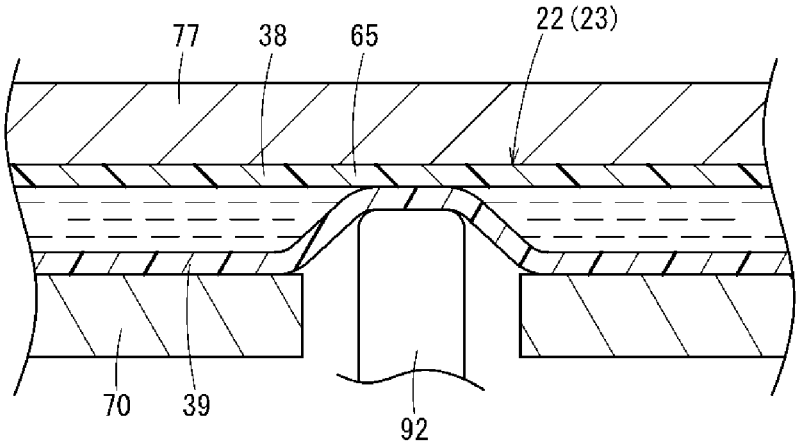
FIG. 5B is a second view for describing the function of the clamp provided at the centrifuge.

When the clamp 92 moves back as in FIG. 5A, the clamp operation section 65 is not pressed, and the flow path at a portion provided with the clamp operation section 65 is opened. When the clamp 92 protrudes to press the clamp operation section 65 as in FIG. 5B, the cover body 77 and the clamp 92 sandwich and press the clamp operation section 65 such that the flow path at the portion provided with the clamp operation section 65 is closed. When the clamp 92 moves back from the state of FIG. 5B, elastic restoration force of the cassette main body 23 (the clamp operation section 65) restores the clamp operation section 65 to an original shape, and the flow path is opened.

Figure 6:
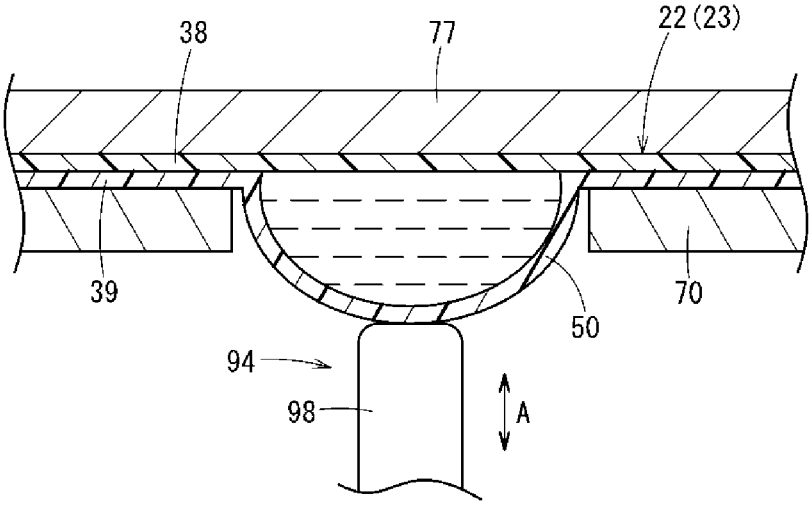
FIG. 6 is a view for describing a function of a centrifugal pressure sensor provided at the centrifuge.

In FIG. 4, the centrifugal pressure sensor 94 is provided at the cassette holding section 90. As illustrated in FIG. 6, the centrifugal pressure sensor 94 has a detection bar 98 configured to contact the balloon section 50 of the cassette 22 held by the cassette holding section 90. The detection bar 98 is movable in the thickness direction (the A direction) of the cassette 22, and is pressed by the balloon section 50 expanding according to the pressure. Consequently, the centrifugal pressure (the pressure in the processing chamber 40) based on the position of the detection bar 98 can be detected.

In FIG. 2, the plurality of pumps 96 are arranged near the cassette holding section 90 with the plurality of pumps 96 being attached to the tubes 20a, 20c, 20i, the second lead tube 48b, and the relay tube 58 connected to the inflow sides of the ACD solution line 45, the introduction line 42, and the second line 52 of the blood component transfer line 43 (also see FIG. 4). In the present embodiment, the pumps 96a to 96d operating on the tubes 20a, 20c, the second lead tube 48b, and the relay tube 58 are in the form of a roller pump configured to circulate liquid (the blood components and the like) in the tubes by repeatedly pressing the tubes.

In FIG. 4, the pumps 96a to 96d in the form of the roller pump each include a rotatably-drivable wheel 100 and rollers 102 rotatably provided at intervals in the circumferential direction at an outer peripheral portion of the wheel 100. Each roller 102 moves in the circumferential direction to crush the tube while the wheel 100 is rotating. Thus, the liquid circulates in the tube.

In the present embodiment, the pumps 96a to 96d in the form of the roller pump are placed such that the rotation axis of each wheel 100 is parallel to an outer housing surface 70a forming the attachment section 76, and the outer peripheral portion of each wheel 100 is partially exposed through the outer housing surface 70a. When the cassette 22 is held by the cassette holding section 90 and the cover body 77 is closed in a state in which the tubes (the tubes 20 and the like) provided with the above-described pump operation sections 64 are placed on the roller pumps (the wheels 100), the tubes (the tubes 20 and the like) are sandwiched between the cover body 77 and each roller pump.

Note that in a variation, the roller pumps (the pumps 96a to 96d) may be placed such that the rotation axis of each wheel 100 is perpendicular to the outer housing surface 70a forming the attachment section 76.

The pump 96e operating on the tube 20i connected to the inflow side of the introduction line 42 is a pump (hereinafter referred to as a "blood sampling pump 96e") configured to extract the blood from the blood donor to transfer the blood to the channel 17 through the introduction line 42. The blood sampling pump 96e may be a roller pump similar to the other pumps 96a to 96d, or may be a pump (a diaphragm pump and the like) in other forms.

Note that when the diaphragm pump is employed as the blood sampling pump 96e, two check valves are provided at an interval at the tube 20i, and a diaphragm portion of the diaphragm pump is connected to the tube 20i between the two check valves. Further, the diaphragm pump can also serve as a donor pressure sensor configured to detect the blood pressure (the donor pressure) of the blood donor based on the amount of displacement of the diaphragm portion.

Figure 7:
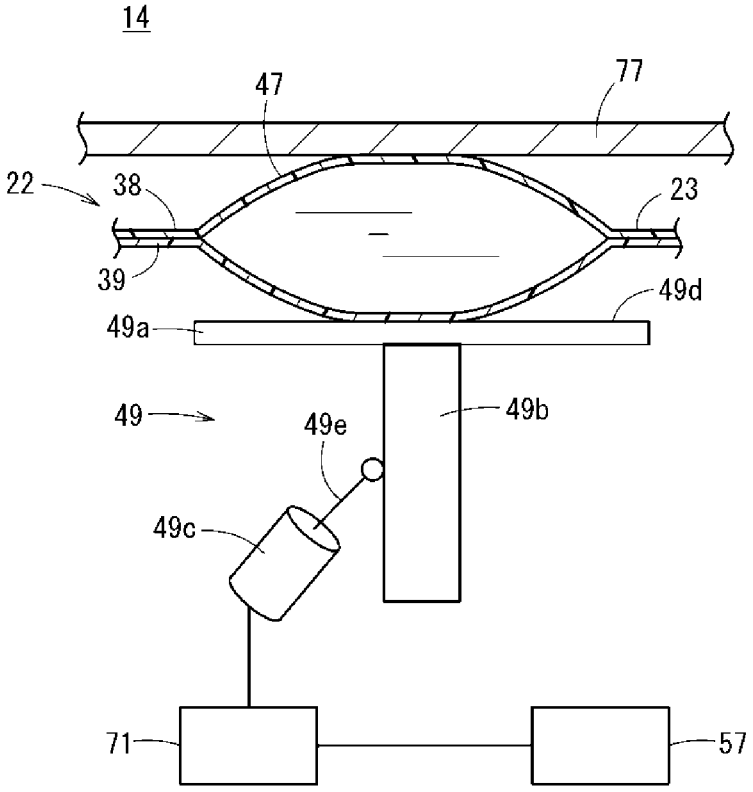
FIG. 7 is a view for describing a function of a retransfusion pump provided at the centrifuge.

The retransfusion pump 49 is configured to return the blood components from the reservoir 47 to the blood donor by pressing the reservoir 47 with the cassette 22 being attached to the attachment section 76. As illustrated in FIG. 7, the retransfusion pump 49 has a pressing plate 49a configured to press the reservoir 47 in the thickness direction, a movable support section 49b configured to support the pressing plate 49a, and a servomotor 49c configured to drive the movable support section 49b.

The pressing plate 49a is displaceable in the thickness direction of the cassette 22. In a state in which the cassette 22 is held by the cassette holding section 90 and the cover body 77 is closed, the pressing plate 49a and the cover body 77 sandwich the reservoir 47, and the pressing plate 49a displaces toward the cover body 77. In this manner, the pressing plate 49a presses the substantially entirety of a liquid housing section of the reservoir 47 in the thickness direction. The pressing plate 49a has a pressing surface 49d configured to contact the reservoir 47 upon pressing of the reservoir 47. In FIG. 7, the pressing surface 49d is formed flat. Note that the pressing surface 49d may be formed in a curved shape.

As illustrated in FIG. 2, the planar shape of the pressing plate 49a is larger than that of the reservoir 47. Thus, the pressing plate 49a can press the substantially entirety of the reservoir 47 from one side (a side close to the second sheet 39) of the reservoir 47 in the thickness direction. The planar shape of the pressing plate 49a may have the substantially same size as that of the reservoir 47.

In FIG. 7, the movable support section 49b protrudes from a back surface (a surface opposite to the pressing surface 49d) of the pressing plate 49a, and is supported to move back and forth in the thickness direction of the cassette 22 by a not-shown guide section provided at the centrifuge 14. The servomotor 49c is configured to drive the movable support section 49b through an optional power transmission mechanism 49e. The servomotor 49c may be a rotary motor or a linear motor.

The servomotor 49c is controlled by a control section 71 provided at the centrifuge 14. The control section 71 is configured to control operation of the retransfusion pump 49 based on the pressure detected by the reservoir pressure sensor 57.

The reservoir pressure sensor 57 is similarly configured as in the above-described centrifugal pressure sensor 94 (see FIG. 6). That is, the reservoir pressure sensor 57 has a detection bar configured to contact the sensor pressing section 61 of the cassette 22 held by the cassette holding section 90. The detection bar is movable in the thickness direction of the cassette 22, and is pressed by the sensor pressing section 61 (see FIG. 3) expanding according to the pressure. Consequently, the inner pressure of the reservoir 47 can be detected based on the position of the detection bar.

Note that the form of the reservoir pressure detection mechanism is not limited to the above-described reservoir pressure sensor 57 pressed by the sensor pressing section 61. For example, a reservoir pressure detection mechanism in another form may be configured to detect the inner pressure of the reservoir 47 based on the torque of the servomotor 49c. In this case, the control section 71 stores a map indicating a relationship between the torque and the inner pressure, and detects the inner pressure of the reservoir 47 with reference to the map.

As illustrated in FIG. 4, one end side of the cover body 77 is rotatably coupled to the device main body 70 through hinge portions 104. The cover body 77 is configured to lock the closed state. The cover body 77 is preferably made of a hard material. Further, when the cover body 77 is made of a transparent material, the cassette/tube assembly 62 attached to the attachment section 76 can be visually checked even in the closed state of the cover body 77, and the state of the cassette/tube assembly 62 can be checked.

Note that the cover body 77 of the illustrated example is configured such that a single plate-shaped body covers a target area. However, according to a variation of the cover body 77, the cover body 77 may have a plurality of plate-shaped bodies (e.g., two bodies) configured to open/close independently, and may be configured to cover the target area with the plurality of plate-shaped bodies.

In FIG. 1, the centrifugal unit 72 has the rotor 78 rotatable about the vertical axis, and a drive section 80 (a motor) configured to rotatably drive this rotor 78. The rotor 78 has an upper rotor 82 to which the channel 17 is attached, and a lower rotor 84 coaxially rotatable with the upper rotor 82. The upper rotor 82 is rotatable relative to the lower rotor 84, and the attachment groove 86 for attachment of the channel 17 is provided at the upper surface 82a of the upper rotor 82.

The lower rotor 84 is coupled to an output shaft of the drive section 80. The upper rotor 82 and the lower rotor 84 are coupled together by a pinion assembly 85 such that the upper rotor 82 rotates at a double speed as compared to that of the lower rotor 84. The pinion assembly 85 has, for example, an intermediate gear supported on the lower rotor 84 to rotate about the axis perpendicular to the rotation axis "a" of the rotor 78, a lower gear provided at a non-rotation portion and configured to engage with a lower portion of the intermediate gear, and an upper gear provided at the upper rotor 82 about the rotation axis "a".

This pinion assembly 85 rotates the upper rotor 82 two times in every rotation of the lower rotor 84. Consequently, even when the channel 17 is continuously rotated by the rotor 78 for centrifugation, twisting among the channel 17 and the plurality of tubes, such as the introduction tube 46, connected to the channel 17 falls within a predetermined range. Thus, a rotary seal between the channel 17 and each of the plurality of tubes such as the introduction tube 46 is not necessary.

The cassette 22 having the above-described configuration can be manufactured by the following manufacturing method, for example. The method for manufacturing the cassette 22 includes the molding process of overlapping the first sheet 38 and the second sheet 39 with each other and welding the first sheet 38 and the second sheet 39 to form the plurality of flow paths between the first sheet 38 and the second sheet 39, thereby molding the cassette 22 including the cassette main body 23; and the sterilization process of sterilizing the cassette 22 obtained by the molding process.

Figure 8:
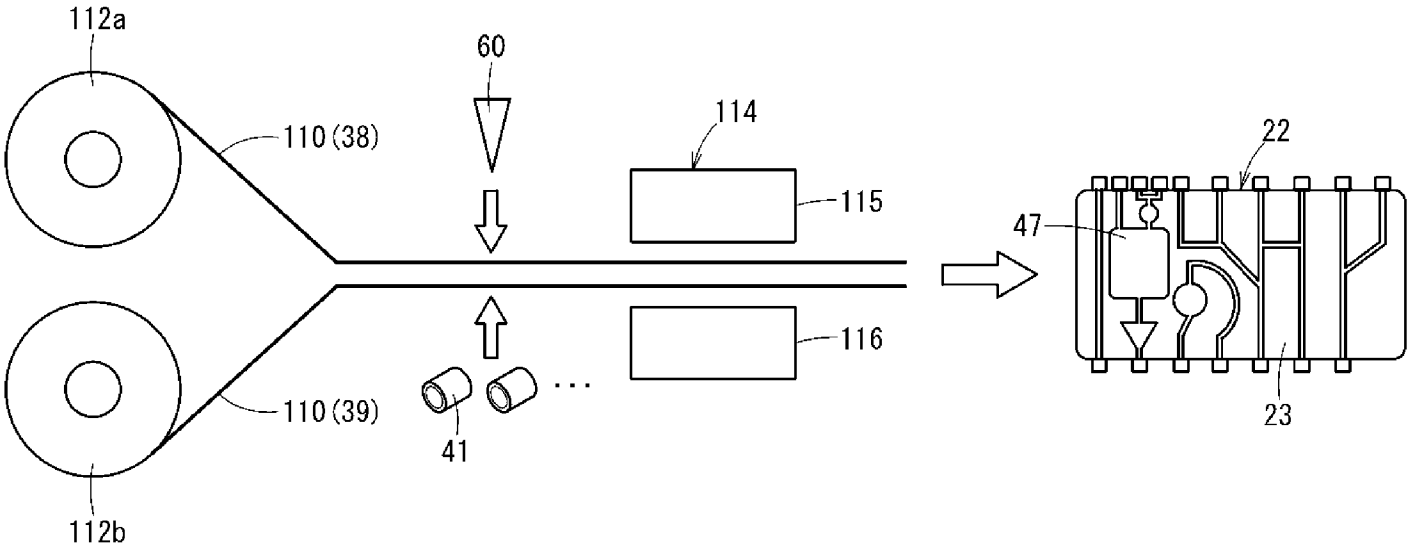
FIG. 8 is a view for describing a molding process in the method for manufacturing the blood component sampling cassette.

As illustrated in FIG. 8, in the molding process, sheet-shaped materials 110 as the materials of the first sheet 38 and the second sheet 39 are, for example, fed from two material rolls 112a, 112b, the sheet-shaped materials 110 each being wound around the material rolls 112a, 112b. The sheet-shaped materials 110 are supplied together with assembly components (the filter member 60, the port members 41) to a bonding device 114 such as a high-frequency fusion device. The bonding device 114 includes upper and lower molds 115 and 116. The bonding device 114 bonds, together with the assembly components, the two overlapping sheet-shaped materials 110, thereby molding the cassette 22 provided with the plurality of flow paths. In this case, upon molding of the cassette 22 by the bonding device 114, the tubes (the tubes 20 and the like) may be connected.

In this molding process, the plurality of flow paths (including the above-described reservoir 47) expanded (protruding) in the thickness direction of the cassette 22 are formed by blow molding. Thus, although not illustrated in detail, the upper and lower molds 115, 116 are provided with grooves corresponding to the shapes of the plurality of flow paths. Upon bonding of the two sheet-shaped materials 110, one or more blow nozzles are sandwiched between the upper and lower molds 115, 116, and then, blow molding gas is blown into between the two sheet-shaped materials 110. Thus, the plurality of flow paths expanding in the thickness direction of the cassette 22 are formed.

In the sterilization process, the cassette 22 obtained by the molding process is subjected to autoclave sterilization. The cassette 22 is made of a material resistant to heat of autoclave sterilization, and therefore, does not melt due to heat in sterilization. Further, the cassette 22 is made of a material exhibiting water vapor permeability, and therefore, water vapor as processing gas for autoclave sterilization is guided into the flow paths of the cassette 22. Consequently, the cassette 22 can be favorably sterilized.

In the sterilization process, the entirety of the blood sampling circuit set 12 including the plurality of bags 18 (the ACD solution bag 24 and the like) may be subjected to autoclave sterilization. Consequently, the blood sampling circuit set 12 can be efficiently sterilized.

Next, features and advantageous effects of the blood component sampling system 10A of the present embodiment configured as described above will be described.

The blood sampling circuit set 12 is attached to the centrifuge 14 as preparation (setup) for blood component sampling from the blood donor by means of the blood component sampling system 10A illustrated in FIG. 1. Specifically, in attachment of the blood sampling circuit set 12 to the centrifuge 14, the cassette/tube assembly 62 is attached to the attachment section 76, the plurality of bags 18 are hung on the centrifuge 14, and the channel 17 is attached to the rotor 78. Meanwhile, the blood donor is punctured with the blood sampling needle 15.

Note that after the cassette/tube assembly 62 has been attached to the attachment section 76, the cover body 77 is closed. Thus, the cassette/tube assembly 62 is sandwiched between the cover body 77 and the attachment section 76, the pump operation sections 64 are set on the pumps 96, and the clamp operation sections 65 are arranged facing the clamps 92.

In FIG. 2, when the user operates the centrifuge 14 to instruct the start of operation of the centrifuge 14, the centrifuge 14 transfers the ACD solution from the ACD solution bag 24 to the ACD solution line 45 in the cassette 22 through the tube 20a under action of the pump 96a, and further supplies the ACD solution to the blood sampling/retransfusion section 16, the introduction line 42, and the channel 17. Thus, blood coagulation in the circuit is prevented.

Next, the centrifuge 14 rotates the rotor 78 to apply the centrifugal force to the channel 17 attached to the rotor 78, and actuates the blood sampling pump 96e to extract the blood (the whole blood) from the blood donor and introduce the blood into the channel 17 through the introduction line 42 and the introduction tube 46. The blood introduced into the channel 17 is separated into the red blood cells, the buffy coat, and the plasma by the centrifugal force while circulating from the one end portion 17a to the other end portion 17b.

The red blood cells separated in the channel 17 are introduced to the first line 51 of the cassette 22 through the first lead tube 48a. Some of the red blood cells are introduced to the red blood cell bag 34 through the tube 20h, and the remaining red blood cells are introduced to the reservoir 47 through the tube 20g. In this case, the centrifuge 14 opens the clamp 92f and closes the clamp 92e, thereby guiding the red blood cells to the red blood cell bag 34 through the flow path elements 51a, 51b. Further, the centrifuge 14 opens the clamp 92e and closes the clamp 92f, thereby guiding the red blood cells to the reservoir 47 through the flow path elements 51a, 51c, the tube 20g, and the flow path element 44b.

The plasma separated in the channel 17 is guided to the second line 52 of the cassette 22 through the second lead tube 48b under action of the pump 96c. Part of the plasma is introduced to the PPP bag 30 through the tube 20d, and the remaining plasma is introduced to the reservoir 47 through the tube 20f. In this case, the centrifuge 14 opens the clamp 92a and closes the clamp 92d among the clamps 92 provided at the second line 52, thereby guiding the plasma to the PPP bag 30 through the flow path elements 52a to 52c. Further, the centrifuge 14 opens the clamps 92c, 92d and closes the clamps 92a, 92b, thereby guiding the plasma to the reservoir 47 through the flow path elements 52a, 52i, 52f, 52g, the tube 20f, and the flow path element 44a.

The buffy coat separated in the channel 17 is introduced to the concentrator 56 through the third lead tube 48c under action of the pump 96d, and then, is separated into the white blood cells and the platelet at the concentrator 56. Further, the separated platelet is guided to the second line 52 of the cassette 22 through the relay tube 58 under action of the pump 96d, and is introduced to the platelet bag 32 through the tube 20e. In this case, the centrifuge 14 opens the clamp 92b and closes the clamps 92c, 92d among the clamps 92 provided at the second line 52, thereby guiding the platelet to the platelet bag 32 through the flow path elements 52e, 52f, 52h.

Further, before or after introduction of the platelet to the platelet bag 32, the platelet preservation solution (the PAS solution) in the platelet preservation solution bag 28 is guided to the second line 52 of the cassette 22 through the tube 20c under action of the pump 96c, and is supplied to the platelet bag 32 through the tube 20e. In this case, the centrifuge 14 opens the clamps 92b, 92d and closes the clamps 92a, 92c among the clamps 92 provided at the second line 52, thereby guiding the platelet preservation solution to the platelet bag 32 through the flow path elements 52d, 52b, 52i, 52h.

The blood components (the red blood cells and the plasma) stored in the reservoir 47 are discharged from the reservoir 47 under action of the retransfusion pump 49 after the centrifugation processing, and then, are returned to the blood donor through the blood sampling/retransfusion section 16 (a retransfusion process). In this case, the foreign material, such as coagulated blood clots, contained in the blood components having passed through the reservoir 47 is trapped by the filter member 60 provided at the retransfusion line 44, and therefore, a risk caused when the foreign material returns to the blood donor can be reduced.

Figure 13A:
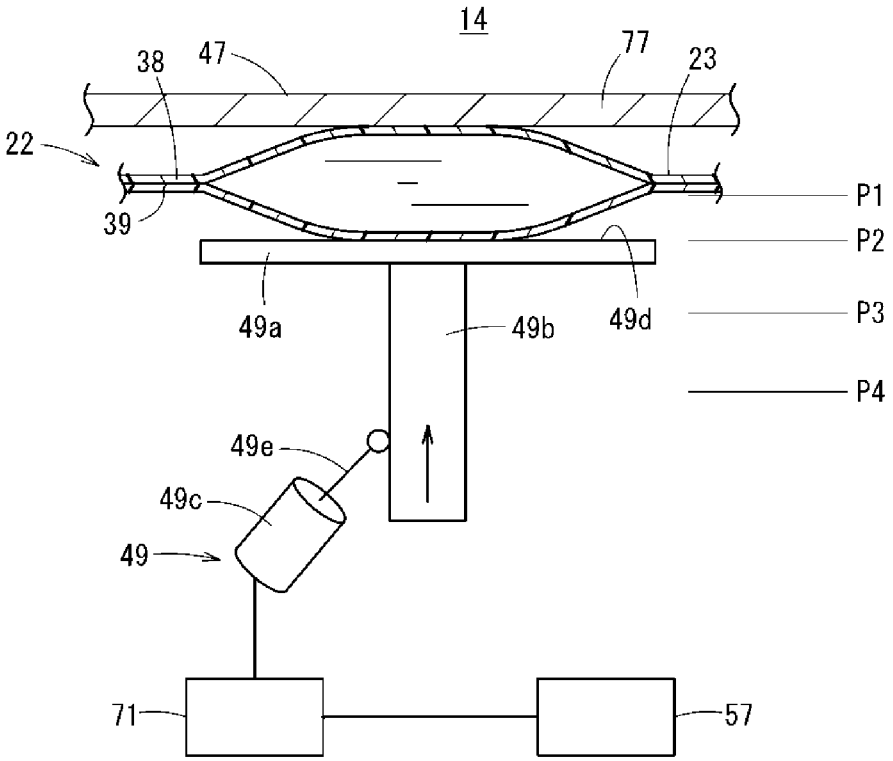
FIG. 13A is a view for describing the operation of the retransfusion pump at an inflow/outflow repeating process in the retransfusion processing.
Figure 14A:
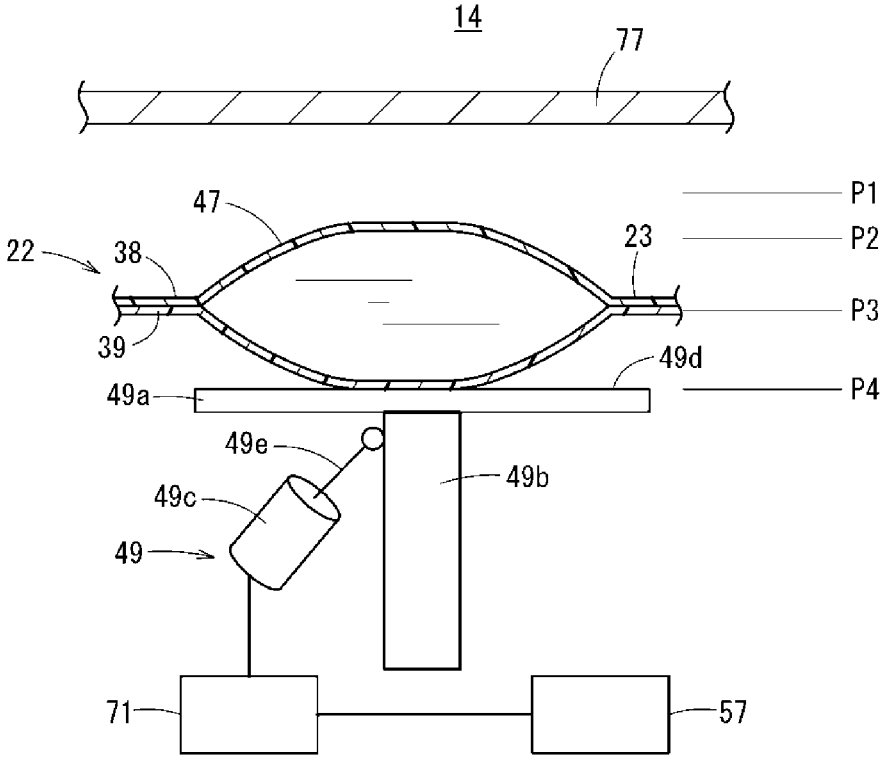
FIG. 14A is a view for describing the operation of the retransfusion pump at a termination process in the retransfusion processing.

Specifically, the retransfusion process includes the priming process (FIG. 9A) of performing air venting from the reservoir 47, the inflow process (FIG. 10A) of causing the blood components to flow into the reservoir 47, the outflow process (FIG. 11A) of causing the blood components to flow out (discharge) from the reservoir 47, the re-inflow process (FIG. 12A) of causing the blood components to re-flow into the reservoir 47, the inflow/outflow repeating process (FIG. 13A) of repeatedly performing inflow and outflow of the blood components, and a termination process (FIG. 14A).

Figure 9A:
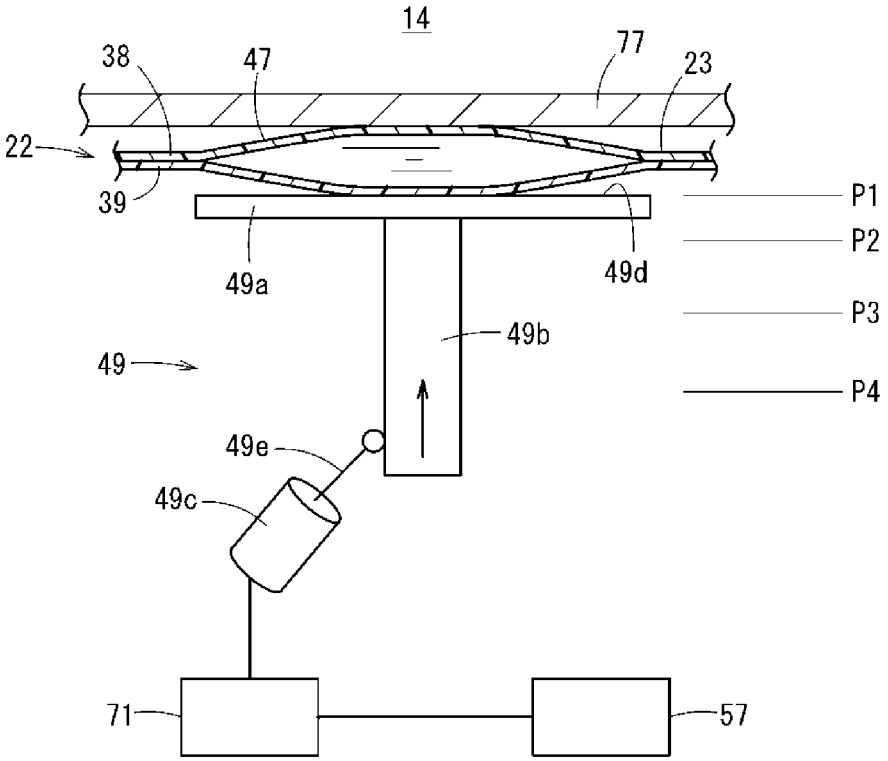
FIG. 9A is a view for describing an operation of the retransfusion pump at a priming process in retransfusion processing.

As illustrated in FIG. 9A, the reservoir 47 is, at the priming process, pressed by the pressing plate 49a, and in this manner, air is removed from the reservoir 47. In this case, the ACD solution is introduced to the reservoir 47 under action of the pump 96a (see FIG. 2) while the pressing plate 49a is being moved to a position P1 for priming under drive action of the servomotor 49c. By introduction of the ACD solution into the reservoir 47 and pressing of the reservoir 47 by the pressing plate 49a, the air in the reservoir 47 is discharged from the reservoir 47 (the air in the reservoir 47 is replaced with the ACD solution).

Figure 9B:
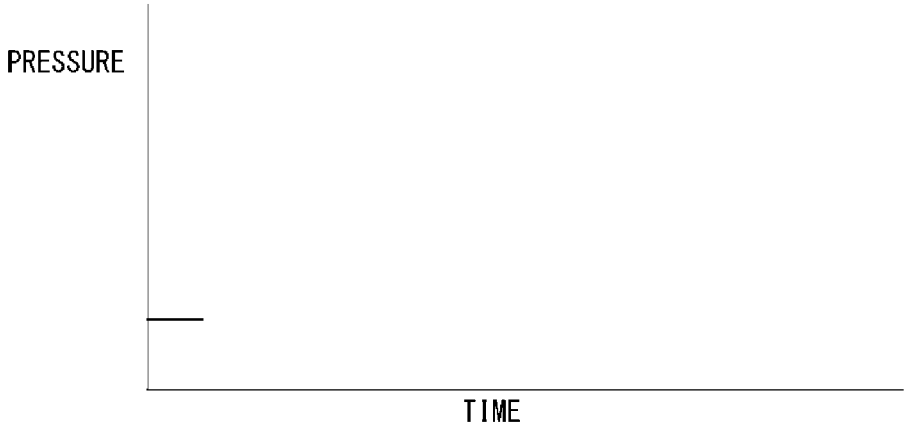
FIG. 9B is a graph of a change in the inner pressure of a reservoir at the priming process.

Note that the discharged air flows through the tube 20b (see FIG. 2), and then, moves into the air bag 26 (see FIG. 2). As illustrated in FIG. 9B, the inner pressure (the pressure detected by the reservoir pressure sensor 57) of the reservoir 47 is substantially constant at a low level at the priming process.

Figure 10A:
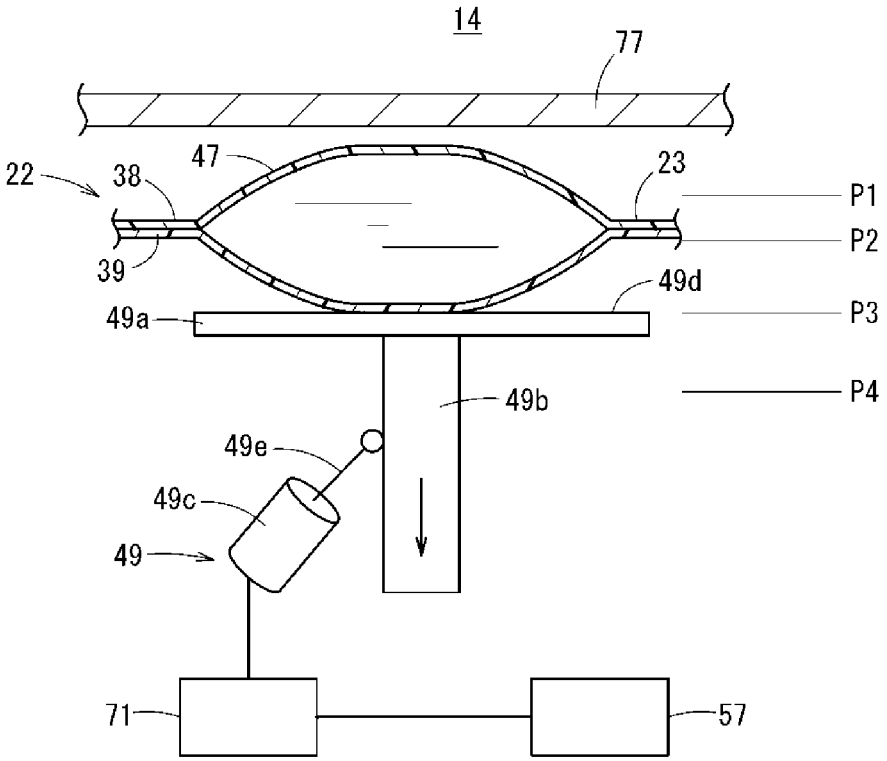
FIG. 10A is a view for describing the operation of the retransfusion pump at an inflow process in the retransfusion processing.

As illustrated in FIG. 10A, the pressing plate 49a is, at the inflow process, lowered (moved in the direction of separating the pressing plate 49a from the cover body 77), and accordingly, the blood components flow into the reservoir 47. In this case, the pressing plate 49a is moved to a position P3 for inflow under drive action of the servomotor 49c. At the position P3, the reservoir 47 is not sandwiched between the cover body 77 and the pressing plate 49a, and therefore, the blood components can flow into the reservoir 47 (the reservoir 47 can be expanded).

Figure 10B:
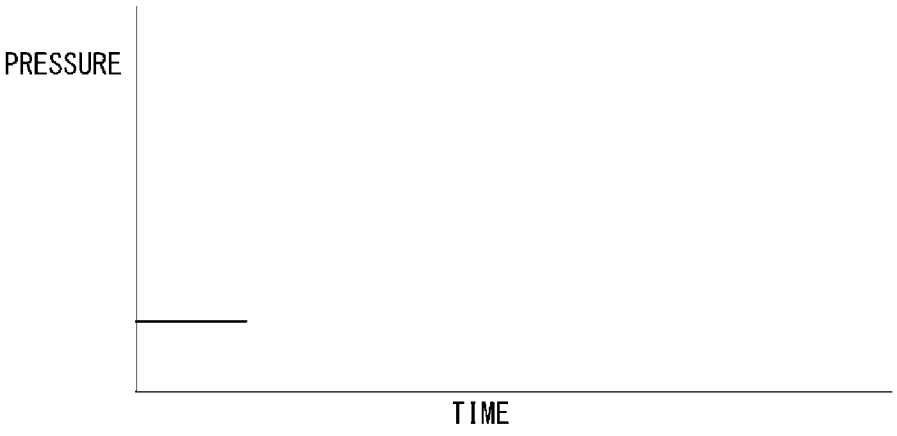
FIG. 10B is a graph of a change in the inner pressure of the reservoir at the inflow process.

This inflow process is continued only for a predetermined set time, and therefore, a predetermined amount of blood components is stored in the reservoir 47. Note that the clamps 92h, 92g (FIG. 2) are closed such that the blood components do not flow out from the reservoir 47. As illustrated in FIG. 10B, the inner pressure of the reservoir 47 is substantially constant at the low level at the inflow process as in the priming process.

Figure 11A:
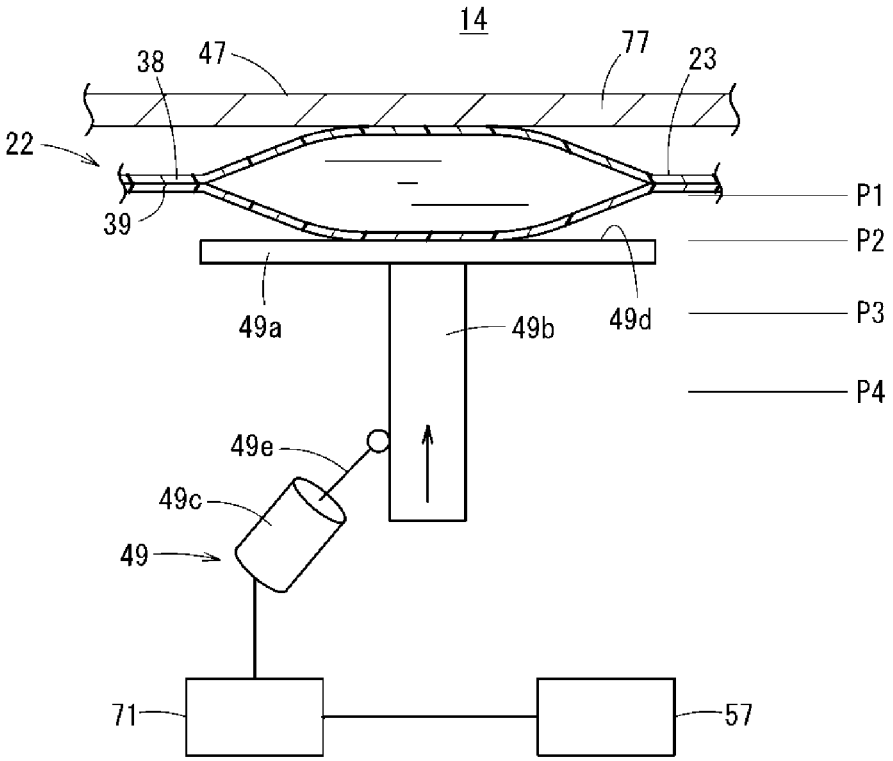
FIG. 11A is a view for describing the operation of the retransfusion pump at an outflow process in retransfusion.

As illustrated in FIG. 11A, the pressing plate 49a is, at the outflow process, lifted (moved close to the cover body 77) to press the reservoir 47, and accordingly, the blood components flow out from the reservoir 47 toward the blood sampling/retransfusion section 16 (FIG. 2). Note that in this case, the clamp 92g (FIG. 2) is opened such that the blood components flow out from the reservoir 47.

Figure 11B:
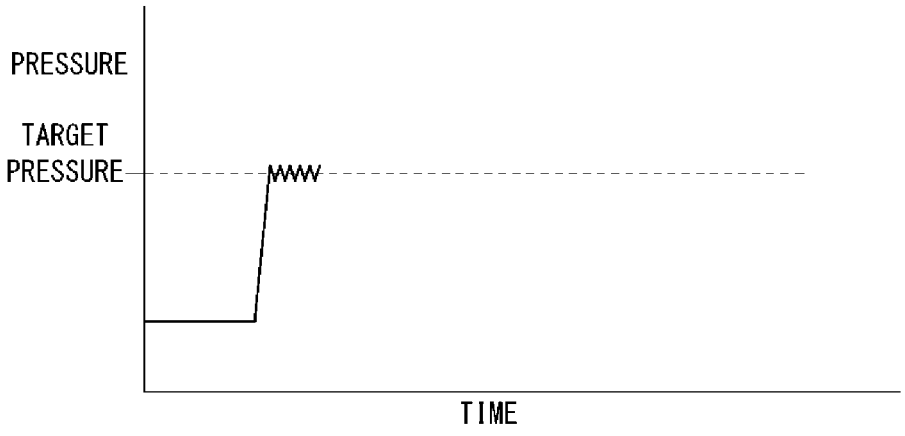
FIG. 11B is a graph of a change in the inner pressure of the reservoir at the outflow process.

At the outflow process, the control section 71 performs feedback control of the servomotor 49c based on the pressure detected by the reservoir pressure sensor 57. Specifically, the control section 71 controls, based on the pressure detected by the reservoir pressure sensor 57, operation of the retransfusion pump 49 (the servomotor 49c) such that the inner pressure of the reservoir 47 reaches a predetermined target pressure (see FIG. 11B). The pressing plate 49a is moved to a position P2 for outflow.

The inner pressure of the reservoir 47 and the outflow speed (the flow rate) of the blood components from the reservoir 47 are proportional to each other. Thus, by feedback control based on the inner pressure of the reservoir 47, the outflow speed of the blood components from the reservoir 47 can be accurately controlled, and the speed (the flow rate) of retransfusion to the blood donor can be maintained substantially constant. Retransfusion to the blood donor is performed with a desired flow rate at a substantially constant speed. Thus, a desired processing efficiency of the centrifugation processing can be ensured while excessive inflow of the ACD solution to the blood donor can be prevented.

Figure 12A:
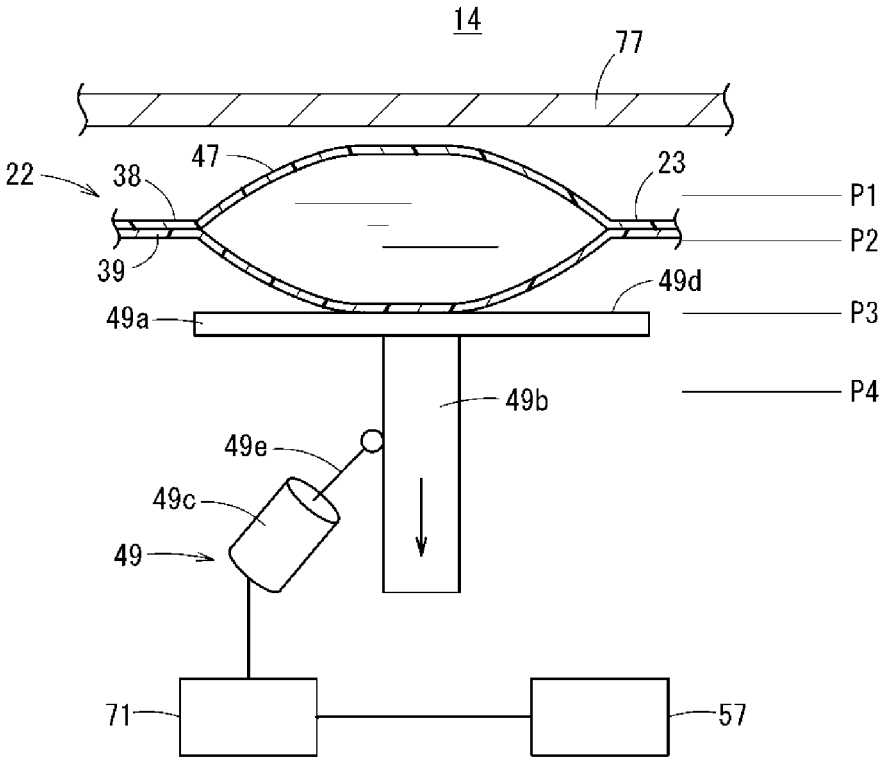
FIG. 12A is a view for describing the operation of the retransfusion pump at a re-inflow process in the retransfusion processing.
Figure 12B:
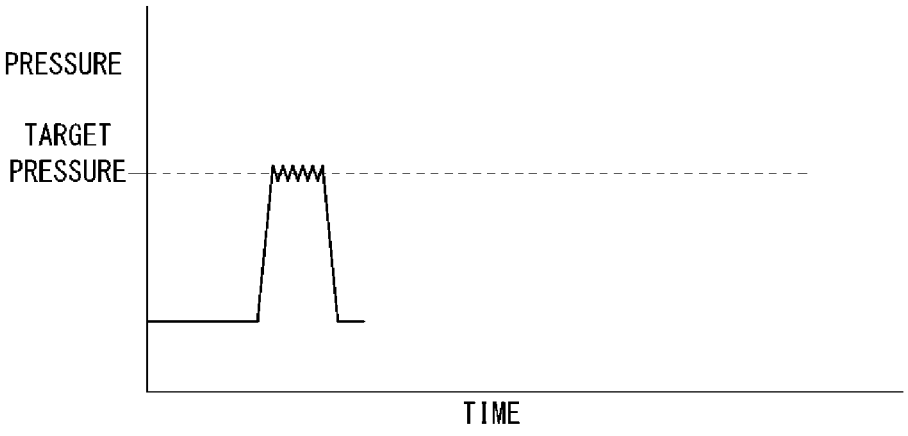
FIG. 12B is a graph of a change in the inner pressure of the reservoir at the re-inflow process.

As illustrated in FIG. 12A, the pressing plate 49a is, at the re-inflow process, lowered, and accordingly, the blood components re-flow into the reservoir 47. In this case, the pressing plate 49a is moved to the position P3 as in the inflow process. The re-inflow process is continued only for the predetermined set time, and therefore, the predetermined amount of blood components is stored in the reservoir 47. The clamps 92h, 92g (FIG. 2) are closed such that the blood components do not flow out from the reservoir 47. As in FIG. 12B, the reservoir 47 is, at the re-inflow process, expanded in association with inflow of the blood components, and therefore, the inner pressure of the reservoir 47 is substantially constant at the low level as in the inflow process.

Figure 13B:
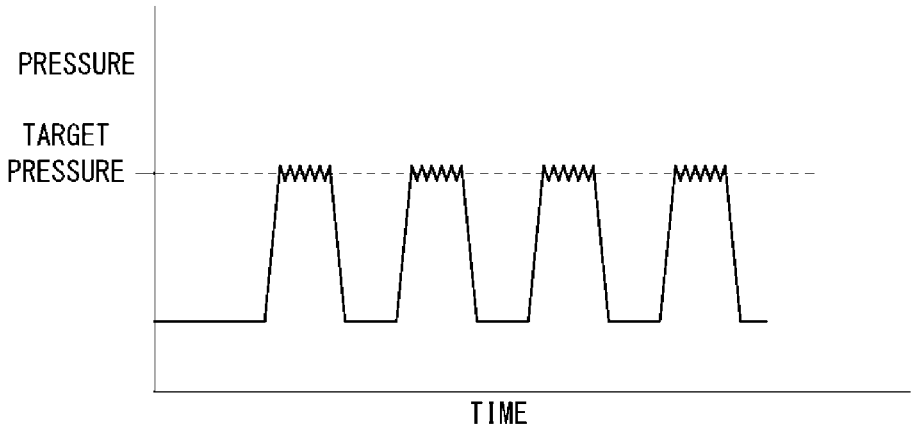
FIG. 13B is a graph of a change in the inner pressure of the reservoir at the inflow/outflow repeating process.

As illustrated in FIG. 13A, the above-described inflow process and the above-described outflow process are repeatedly performed at the inflow/outflow repeating process. The pressing plate 49a is moved between the position P2 and the position P3 under drive action of the servomotor 49c. When the pressing plate 49a is moved from the position P3 to the position P2, the control section 71 performs feedback control of the servomotor 49c based on the pressure detected by the reservoir pressure sensor 57. Thus, as in FIG. 13B, the pressure upon outflow is controlled to substantially constant every time.

Figure 14B:
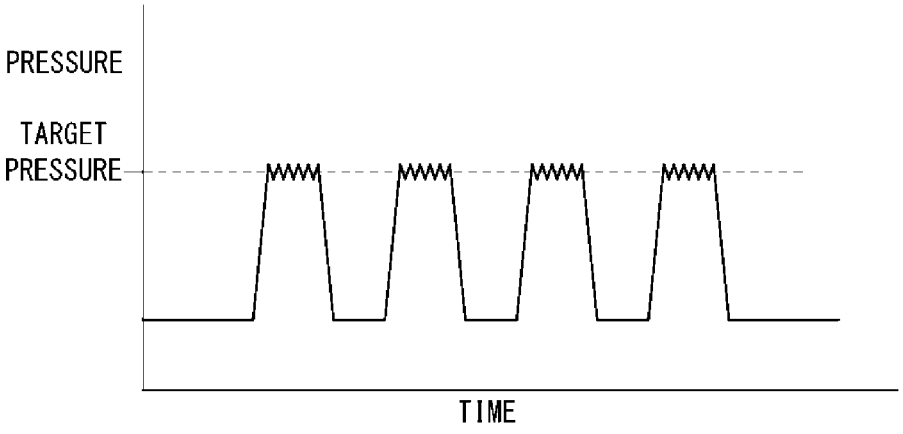
FIG. 14B is a graph of a change in the inner pressure of the reservoir at the termination process.

After outflow (retransfusion operation) of the blood components from the reservoir 47 has been performed a predetermined number of times, the pressing plate 49a is, at the termination process, lowered to a position P4 as in FIG. 14A, thereby detaching the cassette 22 from the centrifuge 14. Thus, the inner pressure of the reservoir 47 decreases as in FIG. 14B.

As described above, according to the cassette 22 of the present embodiment, easier autoclave sterilization as compared to other types of sterilization processing (e.g., EOG sterilization) can be employed as sterilization processing upon manufacturing, leading to efficient manufacturing. Further, the cassette 22 can be manufactured by welding of the first sheet 38 and the second sheet 39 made of the soft materials, and therefore, can be manufactured at lower cost as compared to that of a typical cassette manufactured by injection molding and made of hard resin.

Further, in the present embodiment, the cassette main body 23 is provided with the reservoir 47 pressed by the retransfusion pump 49 of the centrifuge 14 to discharge the blood components. Thus, in the centrifuge 14, it is not necessary to separately ensure a location for disposing the reservoir 47 and a location for providing the retransfusion pump 49, and therefore, device layout simplification and compactification are easily realized. That is, in the centrifuge 14, the location for disposing the reservoir 47 and the location for providing the retransfusion pump 49 are the same as each other, and a common space is used.

In the present embodiment, the cassette main body 23 has the sensor pressing section 61 configured to press the reservoir pressure sensor 57 equipped at the centrifuge 14. Thus, the inner pressure of the reservoir 47 can be detected with a simple configuration. Moreover, the sensor pressing section 61 is provided at the retransfusion line 44, and therefore, the inner pressure of the reservoir 47 can be more precisely detected. In addition, the reservoir 47 is molded by blow molding, and is expanded in the normal state. Thus, a desired reservoir capacity can be easily ensured.

In the present embodiment, the retransfusion pump 49 has the pressing plate 49a configured to press the reservoir 47 in the thickness direction. By the retransfusion pump 49 (a pressing plate type pump) having such a configuration, the substantially entirety of the reservoir 47 can be simultaneously pressed in the thickness direction, and therefore, desired solution transfer performance (the flow rate) can be easily obtained.

In the present embodiment, the centrifuge 14 has the reservoir pressure detection mechanism (the reservoir pressure sensor 57) configured to detect the inner pressure of the reservoir 47, and the control section 71 configured to control operation of the retransfusion pump 49 based on the pressure detected by the reservoir pressure detection mechanism. Thus, the speed (the flow rate) of retransfusion to the blood donor can be accurately controlled. In addition, the control section 71 controls operation of the retransfusion pump 49 such that the inner pressure of the reservoir 47 reaches the predetermined target pressure, and therefore, the speed of retransfusion to the blood donor can be maintained substantially constant.

Second Embodiment

Figure 15:
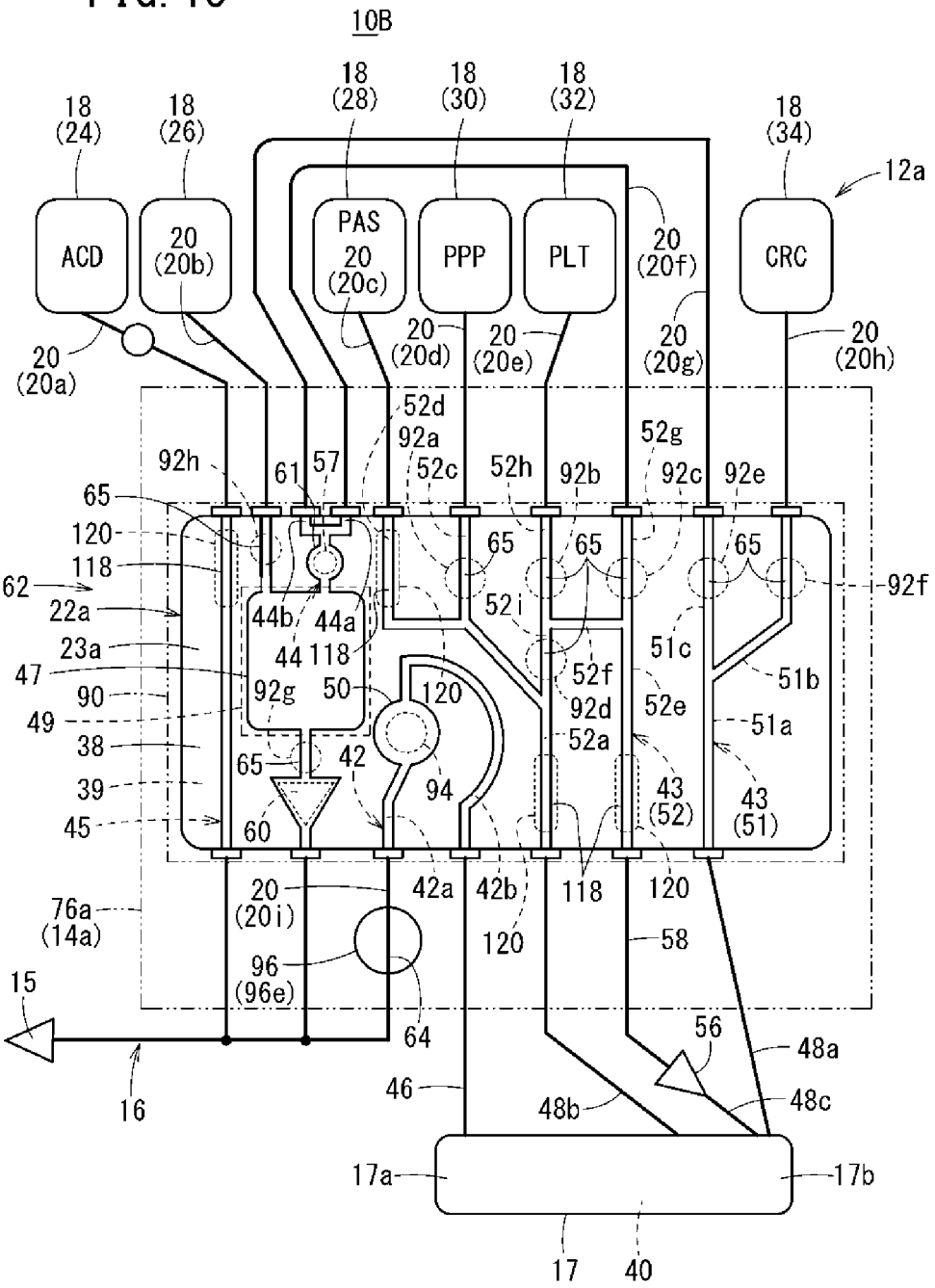
FIG. 15 is a circuit configuration diagram of a blood component sampling system of a second embodiment of the present invention.

Next, differences of a blood component sampling system 10B of the second embodiment of the present disclosure illustrated in FIG. 15 from the blood component sampling system 10A of the first embodiment will be mainly described. This blood component sampling system 10B includes a blood sampling circuit set 12a having a blood component sampling cassette 22a (hereinafter referred to as a "cassette 22a"), and a centrifuge 14a (see FIG. 16) to which the blood sampling circuit set 12a is attached.

The blood sampling circuit set 12a has a cassette main body 23a provided with a plurality of flow paths, and the cassette main body 23a is bonded such that a first sheet 38 and a second sheet 39 overlap with each other in a thickness direction and that the plurality of flow paths are formed. As in the plurality of flow paths of the cassette main body 23 of the first embodiment, the plurality of flow paths of the cassette main body 23a include an introduction line 42, a blood component transfer line 43, a retransfusion line 44, and an ACD solution line 45.

Pump operation sections 118 on which pumps 120 of the centrifuge 14a operate are provided in a region on inflow sides of the plurality of flow paths (excluding the retransfusion line 44) at the cassette main body 23a. In the present embodiment, the pump operation sections 118 are provided in an upstream region of the ACD solution line 45 and an upstream region of a second line 52 (upstream regions of flow path elements 52a, 52d, 52e).

Of flow path formation portions at the cassette main body 23a, at least a pump operation section 64 is expanded in a shape raised in the thickness direction of the cassette main body 23a in a normal state in which a positive pressure is not applied. Note that a downstream portion of the pump operation section 64 of the flow path formation portions at the cassette main body 23a is substantially flat in the normal state in which the positive pressure is not applied, but may be formed to expand in the raised shape when the positive pressure is applied.

Figure 16:
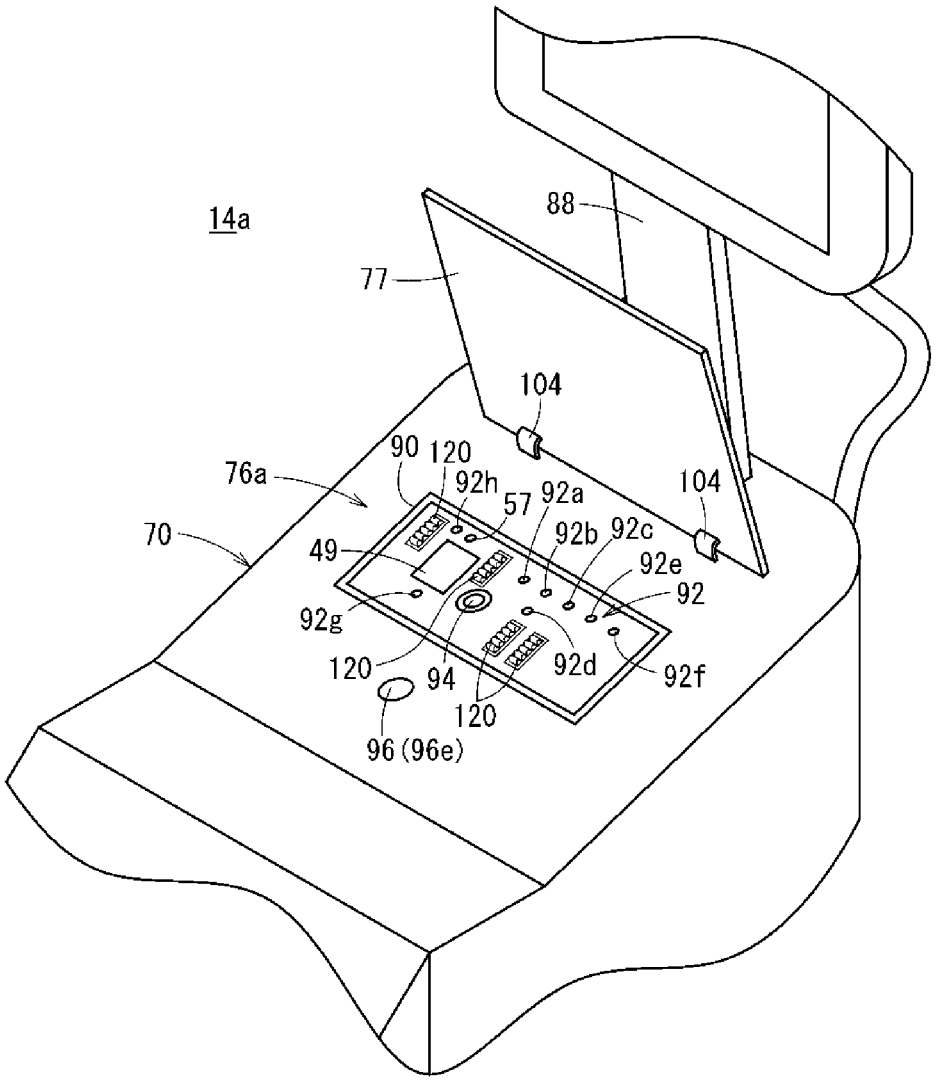
FIG. 16 is a perspective view of a configuration of an attachment section of a centrifuge in the blood component sampling system illustrated in FIG. 15.

As illustrated in FIGS. 15 and 16, an attachment section 76a of the centrifuge 14a includes the pumps 120 arranged at a cassette holding section 90 instead of the pumps 96 at the centrifuge 14 of the first embodiment. Each pump 120 is configured to press the pump operation sections 118 of the cassette 22a held by the cassette holding section 90, thereby circulating liquid (blood components and the like) in the cassette 22a.

Figure 17:
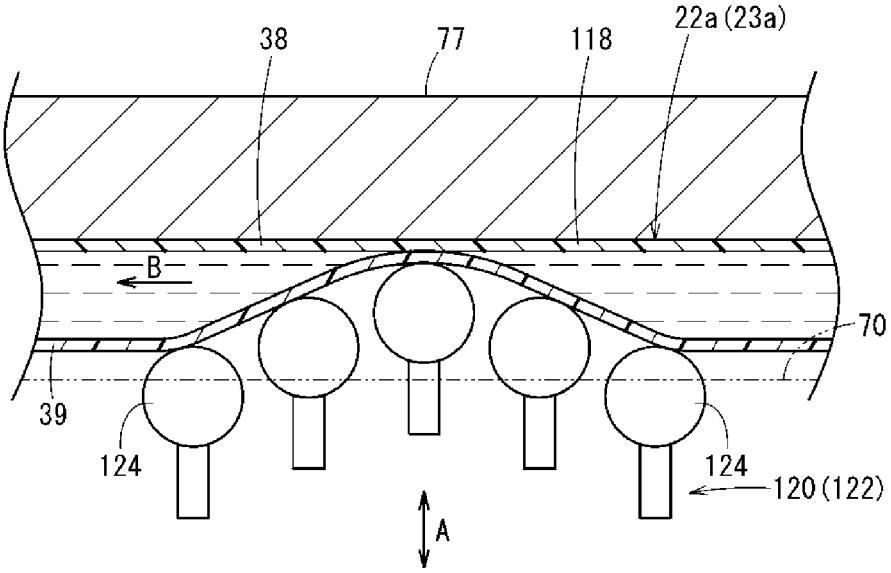
FIG. 17 is a view for describing a function of a finger pump provided at the centrifuge.

In the present embodiment, as illustrated in FIG. 17, the pumps 120 are in the form of a finger pump 122 having a plurality of finger portions 124 (movable pressing bodies). The plurality of finger portions 124 are configured to move back and forth in the thickness direction (a direction indicated by an arrow A) of the cassette 22a attached to the attachment section 76a. The finger pump 122 sequentially shifts, from right to left as viewed in FIG. 17, a position at which the pump operation section 118 is crushed by the plurality of finger portions 124, and therefore, can circulate fluid in a direction indicated by an arrow B. By actuation of the pump 120, the positive pressure is applied to the downstream side of the pump 120 in each flow path (the ACD solution line 45, the second line 52) formed in the cassette main body 23a.

According to the cassette 22a configured as described above, the cassette 22a can be, as in the cassette 22 of the first embodiment, efficiently manufactured at low cost, and no trouble is caused in transfer of fluid such as blood without closing the flow paths formed in the cassette main body 23a upon pump actuation. Further, according to the cassette 22a of the present embodiment, the pump operation sections 118 are automatically set on the pumps 120 when the cassette 22a is attached to the centrifuge 14a, and therefore, the cassette 22a can be more efficiently attached to the centrifuge 14a.

Note that contents of the second embodiment common to those of the first embodiment provide features and advantageous effects identical or similar to those of the first embodiment.

The present disclosure is not limited to the above-described embodiments, and various modifications can be made without departing from the gist of the present disclosure.

In various embodiments described above, the blood has been described as a biological component, but the present disclosure is not limited to the blood. For example, the present disclosure is also applicable to various cells sampled or cultured from patients or donors, and medical liquid including medical agents to be administered to patients and the like.

REFERENCE SIGNS LIST

10A, 10B Blood component sampling system
12, 12a Blood sampling circuit set
14, 14a Centrifuge
22, 22a Cassette
23, 23a Cassette main body
38 First sheet
39 Second sheet
42 Introduction line
43 Blood component transfer line
44 Retransfusion line
47 Reservoir
49 Retransfusion pump
57 Reservoir pressure sensor
61 Sensor pressing section
71 Control section

The invention claimed is:

1. A biological component sampling cassette, comprising:

a cassette main body provided with a plurality of flow paths that are blow molded *or fusion bonded*, wherein the cassette main body is configured to be attachable to a separation device that separates a biological component from liquid containing at least one biological component, wherein the cassette main body comprises a first sheet of a soft resin to which heat sterilization is applicable and a second sheet of said soft resin, said first and second sheets being bonded to each other to form said plurality of flow paths, wherein the plurality of flow paths includes:

an introduction line configured to introduce the liquid, a biological component transfer line configured to transfer, to a sampling container, the biological component obtained by separation processing of the liquid, and a return line configured to transfer *return* liquid *including liquid* other than the biological component obtained by separation processing with the separation device, wherein the return line is provided with a reservoir configured to temporarily store the *return* liquid[to be returned], wherein the cassette main body includes a sensor pressing section that presses a reservoir pressure sensor to thereby detect an inner pressure of the reservoir, wherein the sensor pressing section is located in a portion of the return line that is connected between the reservoir and first and second port members of the cassette main body that connect to respective external tubes, wherein the first port member and the second port member are at an edge of the cassette main body and adjacent to one another in a first direction that is perpendicular to a second direction, wherein the sensor pressing section is between the edge of the cassette main body and the reservoir along the second direction, and wherein the reservoir is configured to be expandable and contractable, and is pressed by a return pump provided at the separation device to discharge the *return* liquid from the reservoir.

2. The biological component sampling cassette according to claim 1, wherein the first port member and the second port member are immediately adjacent to one another.

3. The biological component sampling cassette according to claim 2, wherein the first port member is connected to a first flow path of the plurality of flow paths and the second port member is connected to a second flow path of the plurality of flow paths, wherein the first flow path and the second flow path branch from a third flow path connected to the sensor pressing section.

4. The biological component sampling cassette according to claim 1, wherein the reservoir is expanded in an unpressed state.

5. The biological component sampling cassette according to claim 1, wherein red blood cells flow to the reservoir through the first port member, and wherein plasma flows to the reservoir through the second port member.

6. The biological component sampling cassette according to claim 1, wherein said cassette main body further comprises a filter member between said first and second sheets, said filter member being in fluid communication with and downstream from said reservoir.

7. The biological component sampling cassette according to claim 1, wherein said flow paths are open when positive pressure is not applied.

8. The biological component sampling cassette according to claim 1, wherein said flow paths are closed when positive pressure is not applied.

9. The biological component sampling cassette according to claim 1, wherein the reservoir is defined by part of the first sheet and part of the second sheet, and wherein the part of the first sheet and the part of the second sheet both flex when pressed by the return pump to discharge the *return* liquid from the reservoir.

10. A biological component sampling circuit set comprising:

a biological component sampling cassette including a cassette main body provided with a plurality of flow paths that are blow molded *or fusion bonded*, wherein the cassette main body is configured to be attachable to a separation device that separates a biological component from liquid containing at least one biological component;

a separation processing section connected to the biological component sampling cassette through a first tube and having a processing chamber configured to separate the liquid into multiple biological components by actuation of the separation device; and a bag connected to the biological component sampling cassette through a second tube, wherein the cassette main body comprises a first sheet of a soft resin to which heat sterilization is applicable and a second sheet of said soft resin, said first and second sheets being bonded to each other to form said plurality of flow paths, wherein the plurality of flow paths includes:

an introduction line configured to introduce the liquid;

a biological component transfer line configured to transfer, to a sampling container, the biological component obtained by separation processing of the liquid; and a return line configured to transfer *return liquid including* liquid other than the biological component obtained by separation processing with the separation device, wherein the return line is provided with a reservoir configured to temporarily store the *return* liquid[to be returned], wherein the cassette main body includes a sensor pressing section that presses a reservoir pressure sensor to thereby detect an inner pressure of the reservoir, wherein the sensor pressing section is located in a portion of the return line that is connected between the reservoir and first and second port members of the cassette main body that connect to respective external tubes, wherein the first port member and the second port member are at an edge of the cassette main body and adjacent to one another in a first direction that is perpendicular to a second direction, wherein the sensor pressing section is between the edge of the cassette main body and the reservoir along the second direction, and wherein the reservoir is configured to selectively expand or contract, and is pressed by a return pump provided at the separation device to discharge the *return* liquid from the reservoir.

11. The biological component sampling circuit set according to claim 10, wherein the first port member is connected to a first flow path of the plurality of flow paths and the second port member is connected to a second flow path of the plurality of flow paths, wherein the first flow path and the second flow path branch from a third flow path connected to the sensor pressing section.

12. The biological component sampling circuit set according to claim 10, wherein the reservoir is defined by part of the first sheet and part of the second sheet, and wherein the part of the first sheet and the part of the second sheet both flex when pressed by the return pump to discharge the *return* liquid from the reservoir.

13. A biological component sampling system comprising:

a separation device configured to separate a biological component from liquid containing at least one biological component; and a biological component sampling cassette configured to be attachable to the separation device, wherein the biological component sampling cassette includes a cassette main body provided with a plurality of flow paths that are blow molded *or fusion bonded*, wherein the cassette main body comprises a first sheet of a soft resin to which heat sterilization is applicable and a second sheet of said soft resin, said first and second sheets being bonded to each other to form said plurality of flow paths, wherein the plurality of flow paths includes:

an introduction line configured to introduce the liquid;

a biological component transfer line configured to transfer, to a sampling container, the biological component obtained by separation processing of the liquid; and a return line configured to transfer *return liquid including* liquid other than the biological component obtained by separation processing with the separation device, wherein wherein the return line is provided with a reservoir configured to temporarily store the *return* liquid[to be returned], wherein the cassette main body includes a sensor pressing section that presses a reservoir pressure detection mechanism to thereby detect an inner pressure of the reservoir, wherein the sensor pressing section is located in a portion of the return line that is connected between the reservoir and first and second port members of the cassette main body that connect to respective external tubes, wherein the first port member and the second port member are at an edge of the cassette main body and adjacent to one another in a first direction that is perpendicular to a second direction, wherein the sensor pressing section is between the edge of the cassette main body and the reservoir along the second direction, and wherein the reservoir is configured to selectively expand or contract, and is pressed by a return pump provided at the separation device to discharge the *return* liquid from the reservoir.

14. The biological component sampling system according to claim 13, wherein the return pump equipped at the separation device has a pressing plate configured to press the reservoir in a thickness direction.

15. The biological component sampling system according to claim 14, wherein the separation device includes:

the reservoir pressure detection mechanism configured to detect the inner pressure of the reservoir; and a control section configured to control the return pump based on the inner pressure detected by the reservoir pressure detection mechanism.

16. The biological component sampling system according to claim 15, wherein the control section controls the return pump such that the inner pressure of the reservoir reaches a predetermined target pressure.

17. The biological component sampling system according to claim 15, wherein the first port member and the second port member are immediately adjacent to one another, wherein the first port member is connected to a first flow path of the plurality of flow paths and the second port member is connected to a second flow path of the plurality of flow paths, and wherein the first flow path and the second flow path branch from a third flow path connected to the sensor pressing section.

18. The biological component sampling system according to claim 13, further comprising a cover body coupled to said separation device and configured to close over said cassette main body, said cover body having a holding section configured to engage a peripheral edge of said cassette main body.

19. The biological component sampling system according to claim 13, wherein the reservoir is defined by part of the first sheet and part of the second sheet, and wherein the part of the first sheet and the part of the second sheet both flex when pressed by the return pump to discharge the *return* liquid from the reservoir.

20. The biological component sampling system according to claim 18, wherein said holding section comprises a peripheral edge of said cover body configured to sandwich said peripheral edge of said cassette main body against said separation device.

* * * * *